(12) United States Patent
Zikorus et al.

(10) Patent No.: US 7,842,076 B2
(45) Date of Patent: Nov. 30, 2010

(54) SYSTEMS AND METHODS FOR TREATING A HOLLOW ANATOMICAL STRUCTURE

(75) Inventors: Arthur W. Zikorus, San Jose, CA (US); Robert Gordon McRae, San Jose, CA (US); Michael S. Mirizzi, San Jose, CA (US)

(73) Assignee: Tyco Healthcare Group, LP, Mansfield, MA (US)

( * ) Notice: Subject to any disclaimer, the term of this patent is extended or adjusted under 35 U.S.C. 154(b) by 1073 days.

(21) Appl. No.: 11/313,512

(22) Filed: Dec. 20, 2005

(65) Prior Publication Data

US 2006/0142824 A1  Jun. 29, 2006

Related U.S. Application Data

(60) Provisional application No. 60/637,950, filed on Dec. 20, 2004.

(51) Int. Cl.
*A61F 7/00* (2006.01)
(52) U.S. Cl. .................. 607/96; 607/102; 606/41
(58) Field of Classification Search .......... 606/27, 606/28, 34, 35, 41
See application file for complete search history.

(56) References Cited

U.S. PATENT DOCUMENTS

| 5,556,396 | A | 9/1996 | Cohen |
| 5,584,830 | A | 12/1996 | Ladd |
| 5,722,975 | A | 3/1998 | Edwards et al. |
| 5,743,903 | A | 4/1998 | Stern et al. |
| 5,837,003 | A | 11/1998 | Ginsburg |
| 5,843,152 | A | 12/1998 | Tu et al. |
| 6,066,139 | A | 5/2000 | Ryan et al. |
| 6,183,468 | B1 | 2/2001 | Swanson et al. |
| 6,228,080 | B1 | 5/2001 | Gines |
| 6,235,024 | B1 | 5/2001 | Tu |

(Continued)

FOREIGN PATENT DOCUMENTS

WO  WO 93/08755  5/1993

(Continued)

OTHER PUBLICATIONS

Proebstle et al., Endovenous treatment of the greater saphenous vein with a 940-nm diode laser: Thrombotic occlusion after edoluminal thermal damage by laser-generated steam bubbles, Journal of Vascular Surgery, Apr. 2002, vol. 34, No. 4, p. 729-736.

(Continued)

*Primary Examiner*—Thomas J Sweet
*Assistant Examiner*—Amanda Scott
(74) *Attorney, Agent, or Firm*—Knobbe, Martens, Olson & Bear, LLP

(57) ABSTRACT

A treatment system for occluding a hollow anatomical structure comprises a treatment device sized for insertion into a hollow anatomical structure. The treatment device comprises a therapeutic element configured to treat the hollow anatomical structure. The system comprises a sensor configured to sense a first treatment parameter. A controller is in communication with the treatment device and with the sensor. The controller is configured to determine a second treatment parameter based on the first treatment parameter and output the second treatment parameter.

34 Claims, 16 Drawing Sheets

U.S. PATENT DOCUMENTS

| | | | |
|---|---|---|---|
| 6,304,776 | B1 | 10/2001 | Muntermann |
| 6,542,767 | B1* | 4/2003 | McNichols et al. .......... 600/407 |
| 6,689,127 | B1 | 2/2004 | Gough et al. |
| 6,752,804 | B2 | 6/2004 | Simpson et al. |
| 6,764,488 | B1 | 7/2004 | Burbank et al. |
| 6,964,661 | B2* | 11/2005 | Rioux et al. .................. 606/41 |
| 2001/0041888 | A1 | 11/2001 | Goldman |
| 2003/0109802 | A1 | 6/2003 | Laeseke et al. |
| 2004/0010289 | A1 | 1/2004 | Biggs et al. |
| 2004/0054363 | A1 | 3/2004 | Vaska et al. |
| 2004/0199151 | A1 | 10/2004 | Neuberger |
| 2007/0049999 | A1 | 3/2007 | Esch et al. |
| 2007/0050000 | A1 | 3/2007 | Esch et al. |
| 2007/0055326 | A1 | 3/2007 | Farley et al. |
| 2007/0055327 | A1 | 3/2007 | Esch et al. |
| 2007/0100405 | A1 | 5/2007 | Thompson et al. |
| 2007/0179575 | A1 | 8/2007 | Esch et al. |

FOREIGN PATENT DOCUMENTS

| | | |
|---|---|---|
| WO | WO 97/40882 A | 11/1997 |
| WO | WO 99/11185 | 3/1999 |
| WO | WO 03/049631 A | 6/2003 |
| WO | WO 2004/093693 | 11/2004 |

OTHER PUBLICATIONS

Agah, Thesis-Quantitative Characterization of Arterial Tissue Thermal Damage, U. Tex Austin, Aug. 1988.

Aksan et al., Heat Induced Denaturation of Collagenous Tissue, Proceedings of 2002 ASME Int'l Mech. Eng. Cong. & Expo. (IMECE 2002/HTD-21725), Nov. 2002.

Aksan et al., Thermal Damage Prediction for Collagenous Tissues Part I: A Clinically Relevant, Two-Dimensional Numerical Simulation, *Submitted to the ASME J. Biomech. Eng.*, Jan. 2004.

Aksan et al., Thermal Damage Prediction for Collagenous Tissues Part I: A Clinically Relevant Numerical Simulation Incorporating Heating Rate Dependent Denaturation, J. Biomed. Eng., Feb. 2005, vol. 127, p. 85-97.

Aksan et al., Thermomechanical Analysis of Soft Tissue Thermotherapy, *Submitted to ASME Transactions on Biomedical Engineering*, Jun. 26, 2003.

Chen et al., Phenomenological Evolution Equations for Heat-Induced Shrinkage of a Collagenous Tissue, IEEE Transactions Biomed. Eng., Oct. 1998, vol. 45, No. 10, p. 1234-1240.

Henriques et al., Studies of Thermal Injury Part I, Am. J. Pathology, 1947, vol. 23, p. 531-549.

Moritz et al., Studies of Thermal Injury Part II, Am. J. Pathology, Sep. 1947, vol. 23, p. 695-720.

Moritz et al., Studies of Thermal Injury Part III, Am. J. Pathology, Nov. 1947, vol. 23, p. 915-941.

Moritz et al., Studies of Thermal Injury Part IV, Archives of Pathology, abt. 1948, p. 466-488.

Morrison et al., Radiofrequency Closure Treatment of Greater Saphenous Vein Reflux Utilizing Increased Heat and an Increased Pullback Rate, Am. C. Phlebology 16$^{th}$ Ann. Cong., Nov. 2002, p. 162.

Wright et al., Denaturation of Collagen Via Heating, Ann. Rev. Biomed. Eng., 2002, p. 109-128.

Xu et al., Analysis of Thermal Injury Process Based on Enzyme Deactivation Mechanisms, J. Biomed. Eng., Nov. 1995, vol. 117, p. 462-465.

Zikorus et al., Evaluation of Setpoint Temperature and Pullback Speed on Vein Adventitial Temperature During Endovenous Radiofrequency Energy Delivery in an In-Vitro Model, Vascular and Endovascular Surgery, Mar. 2004, p. 167-174, vol. 38, N. 2.

U.S. Appl. No. 12/206,649, filed Sep. 8, 2008, Thompson et al.

International Search Report and Written Opinion for Application No. PCT-US2005-046796 mailed Dec. 5, 2006.

U.S. Appl. No. 11/491,424, filed Jul. 21, 2006, Esch, et al.

Avitall et al, "The Effects of Electrode-Tissue Contact on Radiofrequency Lesion Generation", Dec. 1997, PACE, vol. 20, 2899-2910.

Cao et al, "Using Electrical Impedance to Predict Catheter-Endocardial Contact During RF Cardiac Ablation", Mar. 2002, IEEE Transactions on Biomedical Engineering, vol. 49 No. 3, 247-252.

Zheng et al, "Electrode Impedance: An Indicator of Electrode-Tissue Contact and Lesion Dimenson During RF Cardiac During Linear Ablation", 2000, Journal of Interventional Cardiac Electrophysiology, 645-654.

* cited by examiner

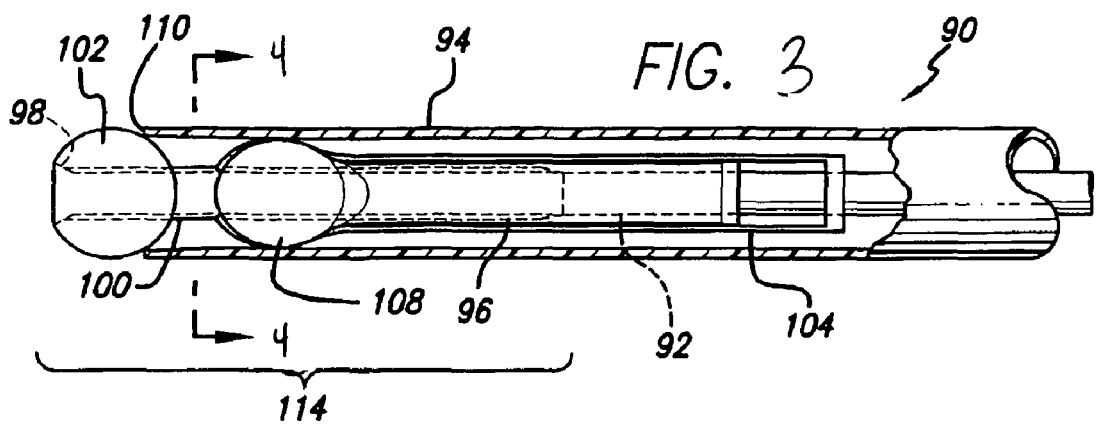
FIG. 3
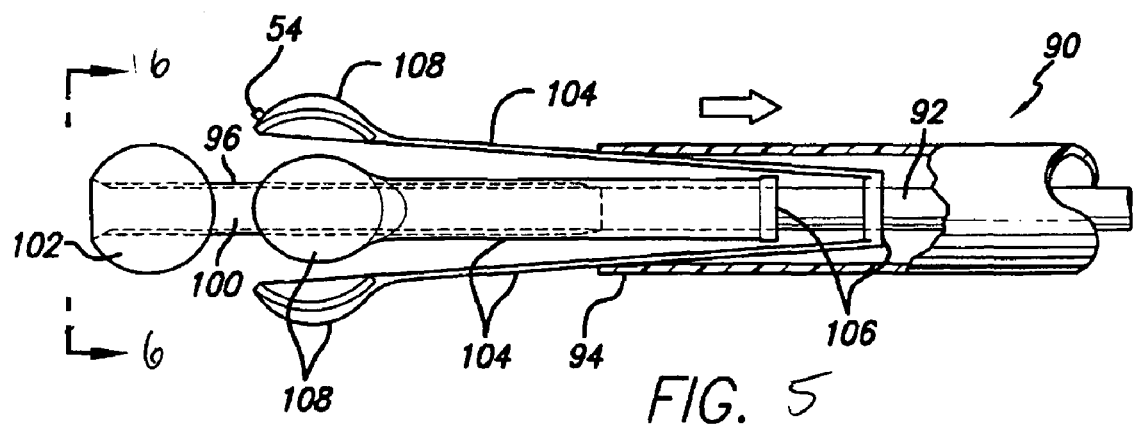
FIG. 5
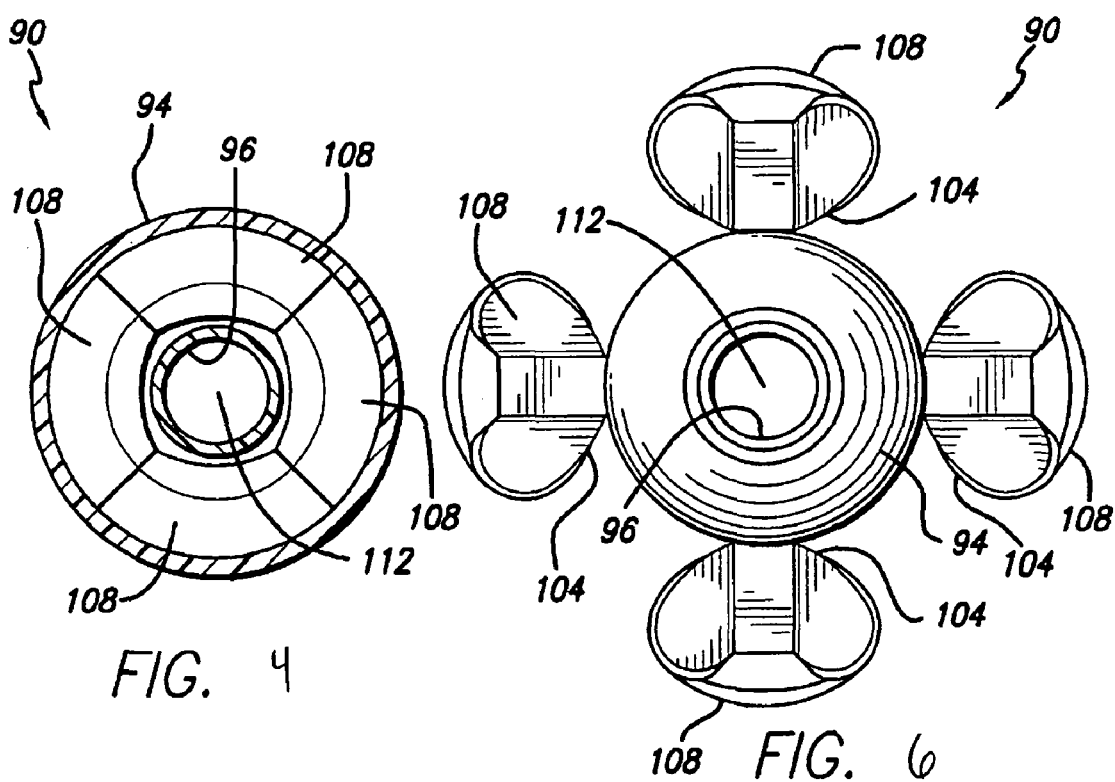
FIG. 4
FIG. 6

SYSTEMS AND METHODS FOR TREATING A HOLLOW ANATOMICAL STRUCTURE

RELATED APPLICATIONS

This application claims the benefit of priority under 35 U.S.C. §119(e) of U.S. Provisional Application No. 60/637,950 filed on Dec. 20, 2004, and entitled "THERMAL REMODELING OF A HOLLOW ANATOMICAL STRUCTURE," which is hereby incorporated herein by reference in its entirety and is to be considered a part of this specification.

BACKGROUND OF THE INVENTION

1. Field of the Invention

Embodiments of the invention relate generally to methods and apparatus for applying energy to constrict and/or shrink a hollow anatomical structure, such as a vein.

2. Description of the Related Art

The human venous system of the lower extremities consists essentially of the superficial venous system and the deep venous system with perforating veins connecting the two systems. The superficial system includes the long or great saphenous vein and the small saphenous vein. The deep venous system includes the anterior and posterior tibial veins which unite to form the popliteal vein, which in turn becomes the femoral vein when joined by the short saphenous vein.

The venous system contains numerous one-way valves for directing blood flow back to the heart. Venous valves are usually bicuspid valves, with each cusp forming a sack or reservoir for blood. Retrograde blood flow forces the free surfaces of the cusps together to prevent continued retrograde flow of the blood and allows only antegrade blood flow to the heart. When an incompetent valve is in the flow path, the valve is unable to close because the cusps do not form a proper seal, and retrograde flow of the blood cannot be stopped. When a venous valve fails, increased strain and pressure occur within the lower venous sections and overlying tissues, sometimes leading to additional, distal valvular failure. Two venous conditions or symptoms which often result from valve failure are varicose veins and more symptomatic chronic venous insufficiency.

SUMMARY OF THE INVENTION

In view of the foregoing, there are disclosed herein systems and methods for ligating and/or substantially occluding a hollow anatomical structure (HAS), such as, for example, a vein. Some of the disclosed devices and systems have a therapeutic element that is capable of directly applying energy to the inner wall of the hollow anatomical structure. Also disclosed are control systems for controlling therapeutic elements to facilitate treatment of hollow anatomical structures.

According to one embodiment, a treatment system for occluding a hollow anatomical structure comprises a treatment device sized for insertion into a hollow anatomical structure. The treatment device comprises a therapeutic element configured to treat the hollow anatomical structure. The system comprises a sensor configured to sense a first treatment parameter. A controller is in communication with the treatment device and with the sensor. The controller is configured to determine a second treatment parameter based on the first treatment parameter and output the second treatment parameter.

According to another aspect, a method of treating a hollow anatomical structure comprises providing a treatment system comprising a catheter having a therapeutic element, a sensor, and a controller in communication with the sensor and the catheter. A first treatment parameter is sensed with the sensor. A second treatment parameter is determined based on the first treatment parameter with the controller.

According to another aspect, a method of treating a hollow anatomical structure comprises providing a treatment device sized for insertion into a hollow anatomical structure having a therapeutic element, a sensor, and a controller in communication with the treatment device and with the sensor. A first parameter is sensed. A thermal injury value based on the sensing of the first parameter is calculated. The thermal injury value is compared to one or more acceptable thermal injury values. A second treatment parameter is determined. The second treatment parameter is output to safely and efficaciously treat the hollow anatomical structure.

For purposes of summarizing the invention, certain aspects, advantages and novel features of the invention have been described herein. It is to be understood that not necessarily all such advantages may be achieved in accordance with any particular embodiment of the invention. Thus, the invention may be embodied or carried out in a manner that achieves or optimizes one advantage or group of advantages as taught herein without necessarily achieving other advantages as may be taught or suggested herein.

BRIEF DESCRIPTION OF THE DRAWINGS

FIG. 3 illustrates a cross-sectional view of the working end of an embodiment of a catheter in accordance with the invention depicting the electrodes in a fully retracted position.

FIG. 4 illustrates an end view of the working end of the embodiment of the catheter taken along line 4-4 of FIG. 3.

FIG. 5 illustrates a cross-sectional view of the working end of the embodiment of the catheter of FIGS. 3 and 4 depicting the electrodes in a fully expanded position.

FIG. 6 illustrates an end view of the working end of the embodiment of the catheter taken along line 6-6 of FIG. 5.

DETAILED DESCRIPTION OF THE PREFERRED EMBODIMENTS

The features of the systems and methods will now be described with reference to the drawings summarized above. The drawings, associated descriptions, and specific implementation are provided to illustrate embodiments of the invention and not to limit the scope of the disclosure.

In addition, methods and functions of treatment systems or devices described herein are not limited to any particular sequence, and the acts or blocks relating thereto can be performed in other sequences that are appropriate. For example, described acts or blocks may be performed in an order other than that specifically disclosed, or multiple acts or blocks may be combined in a single act or block.

Figure 1A:
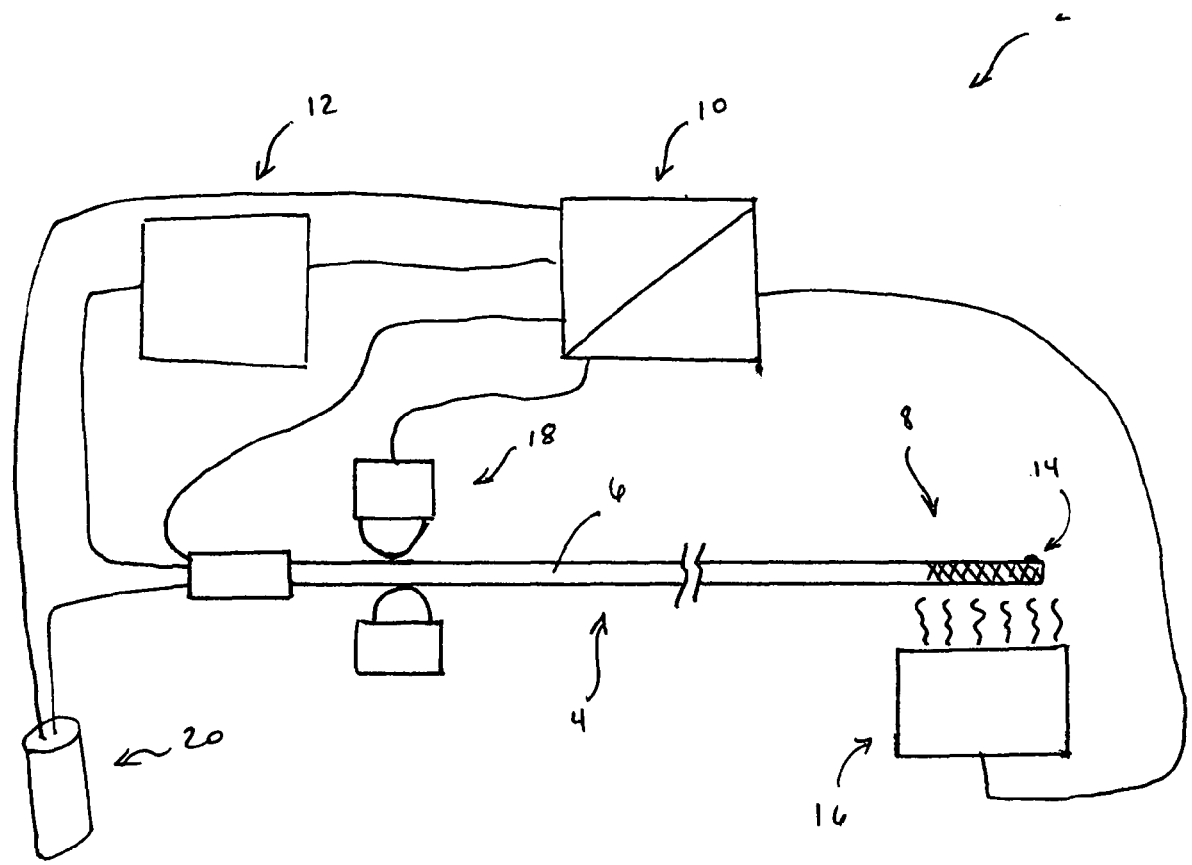
FIG. 1A illustrates an overall view of a treatment system having a therapeutic element and a controller to receive an input from a sensor and to output a control signal to control a parameter of the therapeutic element to treat a hollow anatomical structure, according to an embodiment of the invention.

FIG. 1A illustrates an embodiment of a treatment system 2 for applying energy to a hollow anatomical structure (HAS) (e.g., the wall of the HAS). For example, a HAS may include, but is not limited to, a vein, such as a greater saphenous vein or a varicose vein. In one embodiment, a treatment system 2 comprises a catheter 4, or other treatment device, having an elongate shaft 6 and a therapeutic element 8 located near the distal end of the elongate shaft 6. In some embodiments, the therapeutic element 8 comprises an energy-emission element. In some embodiments, the therapeutic element 8 comprises a fluid dispensing element. The energy-emission element in some embodiments comprises a resistive heating element. In some embodiments, the energy-emission element comprises a radio frequency (RF) emitter element.

The treatment system 2 preferably comprises a controller 10 in communication with the catheter 4. The controller 10 can comprise a processor. In one embodiment, the controller comprises a computer system. The controller can also be in communication with a power source 12. The controller 10 can receive input from a user and/or from other system components, such as, for example, one or more sensors for sensing a characteristic of the therapeutic element or environmental characteristics. The controller can provide an output to a user and/or to other system components to control a characteristic of the therapeutic element.

In some embodiments, the treatment system 2 comprises one or more components for providing an input to the controller 10. In some embodiments, the treatment system 2 comprises a user interface system. Information regarding the treatment environment and/or one or more characteristics of the therapeutic element 8 can be communicated to the controller 10 by the user via the user interface system. For example, in some embodiments, the user can input information regarding the treatment via a keyboard and/or an interactive display, such as, a touch screen system, in communication with the controller 10.

In some embodiments, the treatment system 2 comprises one or more sensors for sensing a characteristic of the therapeutic element. For example, the treatment system can comprise a temperature sensor, a power sensor, a position sensor, a motion sensor, a flow-rate sensor, and/or other sensors for sensing a characteristic of the therapeutic element 8. In some embodiments, a thermocouple 14 can be provided for sensing temperature at the therapeutic element 8. In some embodiments, the system can include a power sensing circuit comprising, for example, a voltage and current sampling device for computing power delivered by a generator and/or power supply 12 to the therapeutic element 8. In some embodiments, an imaging system 16, such as for example an ultrasound or fluoroscopic device can be provided for sensing a relative position of the catheter 4 during treatment. In some embodiments, movement of the catheter can be measured by a suitable sensor. In some embodiments, a positioning element 18, such as, for example, a servo device, can also sense movement or position information. The imaging system 16, position sensor, and/or positioning device 18 can be used to sense the positional velocity (e.g., pullback speed) and/or the dwell time of the catheter 4. Fluid flow from a fluid source 20 can be measured by a flow meter in some embodiments. Although the means to determine positional velocity is described as a sensor, positional velocity information may be encoded in either or both of the sensed generator voltage or current. A suitable means to demodulate the positional velocity from the generator output allows direct measurement of positional velocity without additional sensors for that purpose.

In some embodiments the treatment system 2 comprises one or more sensors for sensing a characteristic of the environment surrounding the catheter. For example, the treatment system can comprise one or more sensors for determining the size, length, and configuration of a treatment site, such as, for example, a sensor for determining the wall thickness and/or length of a HAS to be treated. In other embodiments, environmental characteristics can be input or selected by the user. In some embodiments, environmental characteristics can be known, assumed and/or selected by the controller 10.

In some embodiments, the treatment system 2 comprises one or more components for controlling, adjusting and/or changing a characteristic of the therapeutic element 8. For example, the treatment system 2 can comprise a display or signal in communication with the controller 10 that indicates to a user how to control, adjust, and/or change a characteristic of the therapeutic element to effectively control the use of the treatment system 2. For example, the controller 10 can output a display or a signal to instruct a user to adjust the temperature and/or the power supply to the therapeutic element 8 in one embodiment. In another embodiment, the controller 10 can output a display or a signal to instruct a user to adjust the positional velocity and/or the dwell time of the therapeutic element 8. For example, in one embodiment, the controller 10 can output the current positional velocity and a target positional velocity for the therapeutic element 8. In another embodiment, the controller 10 can output a display or a signal to instruct a user to adjust the flow rate of a fluid dispensed by the treatment system 2.

In some embodiments, the controller 10 can control the temperature and/or the power delivery to the therapeutic element 8 of the catheter 4. The controller 10, in some embodiments, can be in communication with the power supply 12 and/or generator to adjust the temperature and/or power delivery to the therapeutic element of the catheter. In some embodiments, the energy-emission element optionally includes a plurality of emission segments, and each of the segments may be independently operable to emit energy into the surroundings of the energy-emission element, as described in more detail below. The treatment system 2 optionally comprises a power source 12 drivingly connected to the emission segments. In some embodiments, the power source 12 is operable pursuant to a multiplexing algorithm to deliver power to, and operate, the emission segments in a multiplexed fashion. In one embodiment, the energy-emission element comprises a resistive element such as a resistive coil. In another embodiment, the energy-emission element comprises a radio frequency (RF) emitter. In some embodiments, the energy-emission element has an effective axial length along which the energy-emission element emits energy. In certain embodiments, the effective axial length of the energy-emission element is adjustable.

In some embodiments, the controller 10 can control the position and/or movement of the catheter 4. The controller 10, in some embodiments, can be in communication with a positioning device 18 to control the position and/or positional velocity of the catheter 4. The positioning device 18, in some embodiments can include a motor, a servo device, a mechanical arm or linkage, an actuator, a pneumatic and/or hydraulic system, or any other suitable device for controlling the movement or position of the catheter 4. In some embodiments, the positioning device 18 can also comprise a sensor in communication with the controller 10 for sensing the position or movement of the catheter 4.

In some embodiments, the controller 10 can control the flow rate of fluid delivered through the catheter 4 to the treatment site. The controller 10, in some embodiments, can be in communication with the fluid source 20 to control the delivery of the fluid. In some embodiments, it can be advantageous to deliver one or more of the following fluids to the treatment site: saline, a venoconstrictor, sclerosant, high-impedance fluid, adhesive, hydrogel, or the like. Some embodiments comprise one or more of the following exemplary venoconstrictive agents: phenylephrine, high-concentration K+ solution, sumatriptan, dihydroergotamine, 5-hydroxytryptamine (or an equivalent that can bind to 5-HT1 receptors found in the saphenous vein), and other suitable agents.

According to one embodiment, a treatment system comprises a sensor to sense a first treatment parameter. The treatment system comprises a controller in communication with the sensor to determine a second treatment parameter based on the first treatment parameter and output the second treatment parameter. In some embodiments, the first treatment parameter is one of temperature, positional velocity, dwell time, power level and flow rate. In some embodiments, the second treatment parameter is one of temperature, positional velocity, dwell time, power level and flow rate.

For example, in one embodiment, the sensor senses the temperature of the therapeutic element and the controller adjusts the positional velocity of the therapeutic element. In another embodiment, the sensor senses the temperature of the therapeutic element and the controller adjusts the dwell time of the therapeutic element. In another embodiment, the sensor senses the temperature of the therapeutic element and the controller adjusts the flow rate of a fluid dispensed through the therapeutic element.

In another embodiment, the sensor senses the power level delivered by a power source to the therapeutic element and the controller adjusts the positional velocity of the therapeutic element. In another embodiment, the sensor senses the power level delivered by a power source to the therapeutic element and the controller adjusts the dwell time of the therapeutic element. In another embodiment, the sensor senses the power level delivered by a power source to the therapeutic element and the controller adjusts the flow rate of a fluid dispensed through the therapeutic element.

In another embodiment, the sensor senses the positional velocity of the therapeutic element and the controller adjusts the temperature of the therapeutic element. In another embodiment, the sensor senses the positional velocity of the therapeutic element and the controller adjusts the power level delivered by a power source to the therapeutic element. In another embodiment, the sensor senses the positional velocity of the therapeutic element and the controller adjusts the flow rate of a fluid dispensed through the therapeutic element.

In another embodiment, the sensor senses the dwell time of the therapeutic element and the controller adjusts the temperature of the therapeutic element. In another embodiment, the sensor senses the dwell time of the therapeutic element and the controller adjusts the power level delivered by a power source to the therapeutic element. In another embodiment, the sensor senses the dwell time of the therapeutic element and the controller adjusts the flow rate of a fluid dispensed through the therapeutic element.

In another embodiment, the sensor senses the flow rate of a fluid dispensed from the treatment system and the controller adjusts the temperature of the therapeutic element. In another embodiment, the sensor senses the flow rate of a fluid dispensed from the treatment system and the controller adjusts the power level delivered by a power source to the therapeutic element. In another embodiment, the sensor senses the flow rate of a fluid dispensed from the treatment system and the controller adjusts the positional velocity of the therapeutic element. In another embodiment, the sensor senses the flow rate of a fluid dispensed from the treatment system and the controller adjusts the dwell time of the therapeutic element.

One example of a treatment according to one embodiment comprises providing a treatment system 2 for applying energy to a HAS. The treatment system 2 comprises a catheter 4 having an elongate shaft 6 and a therapeutic element 8 located near the distal end of the elongate shaft 6. The therapeutic element 8 is a radio frequency (RF) emitter element. The treatment system 2 also comprises a controller 10 in communication with the catheter 4. The controller 10 is configured to monitor temperature and/or positional velocity using one or more sensors during treatment. In other embodiments, the controller is configured to monitor power output rather than, or in addition to, temperature.

The catheter is inserted into a HAS for treatment. According to one method, a sensor senses the temperature at the intima during treatment and sends a signal to the controller. The controller processes the temperature signal. The controller adjusts the positional velocity of the catheter based on the sensed temperature to achieve a safe and efficacious treatment of the HAS. For example, the controller can send a signal to a servo device to control the movement or position of the catheter. According to another embodiment, the controller can send a signal instructing the user to increase or decrease the positional velocity of the catheter.

According to another method, a position sensor and/or an imaging device senses the positional velocity of the catheter. The position sensor and/or imaging device sends a signal to the controller. The controller processes the positional velocity signal. The controller adjusts the temperature and/or power output of the catheter based on the sensed positional velocity of the catheter to achieve a safe and efficacious treatment of the HAS. For example, the controller can send a signal to the generator and/or power source to increase power delivery by the radio frequency (RF) emitter element.

According to another example of a treatment according to another embodiment comprises providing a treatment system 2 for applying energy to a HAS. The treatment system 2 comprises a catheter 4 having an elongate shaft 6 and a therapeutic element 8 located near the distal end of the elongate shaft 6. The therapeutic element 8 is a resistive heating element. The treatment system 2 also comprises a controller 10 in communication with the catheter 4. The controller 10 is configured to monitor temperature and/or dwell time using one or more sensors during treatment. In other embodiments, the controller is configured to monitor power output rather than, or in addition to, temperature.

The catheter is inserted into a HAS for treatment. According to one method, a sensor senses the temperature at the intima during treatment and sends a signal to the controller. The controller processes the temperature signal. The controller adjusts the dwell time of the catheter based on the sensed temperature to achieve a safe and efficacious treatment of the HAS. For example, the controller can send a signal to a servo device to control the movement or position of the catheter. According to another embodiment, the controller can send a signal instructing the user to increase or decrease the dwell time and/or position of the catheter.

According to another method, a position sensor and/or an imaging device senses the dwell time and/or position of the catheter. The position sensor and/or imaging device sends a signal to the controller. The controller processes the dwell time and/or position signal. The controller adjusts the temperature and/or power output of the catheter based on the sensed dwell time and/or position of the catheter to achieve a safe and efficacious treatment of the HAS. For example, the controller can send a signal to the generator and/or power source to increase power delivery by the resistive heating element.

According to yet another example of a treatment according to another embodiment comprises providing a treatment system 2 for applying energy to a HAS. The treatment system 2 comprises a catheter 4 having an elongate shaft 6 and a therapeutic element 8 located near the distal end of the elongate shaft 6. The therapeutic element 8 comprises a fluid dispensing element. The treatment system 2 also comprises a controller 10 in communication with the catheter 4. The controller 10 is configured to monitor positional velocity and/or fluid flow using one or more sensors during treatment. In other embodiments, the controller is configured to monitor one or more of the other parameters discussed herein.

The catheter is inserted into a HAS for treatment. According to one method, a sensor senses the fluid flow of a fluid, such as, for example, a sclerosant, dispensed into the HAS through the therapeutic element, and sends a signal to the controller. The controller processes the fluid flow signal. The controller adjusts the positional velocity of the catheter based on the sensed fluid flow to achieve a safe and efficacious treatment of the HAS. For example, the controller can send a signal to a servo device to control the movement or position of the catheter. According to another embodiment, the controller can send a signal instructing the user to increase or decrease the positional velocity and/or change the position of the catheter.

According to another method, a position sensor and/or an imaging device senses the positional velocity and/or position of the catheter. The position sensor and/or imaging device sends a signal to the controller. The controller processes the positional velocity and/or position signal. The controller adjusts the fluid flow rate through the therapeutic element based on the sensed positional velocity and/or position of the catheter to achieve a safe and efficacious treatment of the HAS. For example, the controller can send a signal to a pump and/or fluid source to increase or decrease fluid delivery by the fluid dispensing element.

According to yet another example of a treatment according to another embodiment comprises providing a treatment system 2 for applying energy to a HAS. The treatment system 2 comprises a catheter 4 having an elongate shaft 6 and a therapeutic element 8 located near the distal end of the elongate shaft 6. The treatment system 2 also comprises a controller 10 in communication with the catheter 4. The controller 10 is configured to receive an input to the controller 10 through a user interface system. According to one method of treatment, information regarding the treatment environment and/or one or more characteristics of the therapeutic element 8 is be communicated to the controller 10 by the user via the user interface system. For example, environmental characteristics, such as, for example HAS tissue characteristics, size, length, and configuration of a treatment site, can be input or selected by the user. In some embodiments, environmental characteristics can be known, assumed, calculated and/or selected by the controller 10. As will be described further below, in some embodiments, upper and lower thermal injury (TI) values can be determined by the controller, or input by the user. These thermal injury values can be used as boundaries to promote safety and efficacy during treatment. In operation, a value of TI between the upper and lower bounds of safety and efficacy can be determined and/or selected by the controller or input by the user. After a value of TI has been established, other control parameters can be set.

Additional features and advantages of some embodiments are described in more detail below with reference to FIGS. 2-16D.

Some preferred treatments, methods and procedures for using a treatment system provide an improved and generalized treatment to cause a durable change in the shape of a HAS, or to cause a durable occlusion or obliteration of a HAS while minimizing or preventing surrounding tissue damage.

One method of treatment comprises a generalized approach of achieving complete, safe, and effective vessel occlusion. The desired response to the controlled heating of a blood vessel or HAS preferably produces three or more of the following short term effects: inflammation, endothelial denudation, collagen denaturation and contraction, platelet aggregation, thrombosis, and swelling of vessel wall components. These short term effects preferably occur during heating of the HAS or within seconds to hours afterwards. In addition to producing three or more of the preferred short term effects, an appropriate level of heating of the blood vessel preferably also triggers two or more of the following secondary biological responses: proliferation of fibroblasts, proliferation of smooth muscle cells, organization of intramural thrombosis, organized fibrosis, new collagen synthesis, or tissue absorption. These secondary responses may occur days to weeks following initial heating of the HAS.

In some embodiments, the generalized method includes provisions for and relies on acute feedback with relevant treatment parameters, such as: temperature, power, impedance, etc. The measured temperature preferably is at the interface of the treatment device and the vessel intima.

In some embodiments, the adventitia temperature may also be controlled through a function of: intima temperature, electrode mass, electrode area, electrode spacing, vessel wall thickness, vessel thermal properties, duration of intimal heating, and surrounding environmental thermal properties.

During treatment, providing a steep temperature gradient across the vessel wall improves both efficacy and safety. The time-temperature relationship causes both cell necrosis and collagen fibril denaturation. Vascular collagen generally begins to denature at a higher energy level (time accumulation at a given temperature) than is required to cause cell death. However, as both collagen denaturation and cell necrosis are time-temperature dependent, the two distinct responses are linked to one another. Control of both the time and the temperature can be employed to effect both a complete and durable occlusion, as well as surrounding tissue protection. Both cell necrosis and collagen fibril denaturation are effects of thermal damage and/or tissue coagulation. This thermal damage can be described as a rate process using kinetic models. In the standard thermal damage process, the measure of the endpoint damage or Thermal Injury (TI) is expressed as the time integral of the injury accumulation rate and can be calculated from an Arrhenius integral:

$$TI_{(\tau)} = \ln\left[\frac{C(0)}{C(\tau)}\right] = \int_o^\tau Ae^{-[\frac{E}{RT}]}dt$$

Where: TI is the dimensionless value of Thermal Injury, C is the concentration of undamaged tissue, A is the "frequency factor" (1/s)—thermal process rate coefficient determined by tissue type, E is the energy barrier that must be overcome by the native tissue molecules in order to denature (J/mole)—thermal process rate coefficient determined by tissue type, R is the universal gas constant (8.31 J/mole-° K.), T is the absolute temperature (° K.), and τ is the time (s).

The physical significance of the damage parameter or Thermal Injury (TI) is that it is the logarithm of the ratio of original concentration of undamaged tissue to the remaining undamaged tissue at the end of heating. For example, after a heating cycle, a calculated TI value equal to 1 would constitute a level of thermal injury where 36.8% of the native tissue remains undamaged or, contrarily, 63.2% of the native tissue has been thermally injured. Likewise, when TI reaches a value equal to 10, 99.9% of the native tissue has been thermally injured. By adjusting modeling coefficients, calibration of the TI parameter can be achieved to represent full thickness vessel wall injury.

In some embodiments, control of dwell time may be accomplished by controlling the positional velocity, or by modulating the position, of a treatment device that provides a prescribed temperature at the intima. In some embodiments, a prescribed temperature could be a constant intimal temperature or a variable temperature that provides therapeutic shrinkage and damage to the vessel wall. According to some embodiments, one form of heating involves constant temperature of the intima and conduction of the heat at the intimal-lumen interface to the wall of the vessel and surrounding tissues as well as Joule heating which occurs by the conduction of RF throughout the wall and tissues. Overall, this may result in a volumetric heating effect.

In some embodiments, a control system may be implemented by a controller to provide optimal treatment safety and efficacy. In one embodiment, the control system uses control coefficients determined by a look-up table. In another embodiment, the control system uses control coefficients determined by calculation, such as, for example, by real-time calculation. In some embodiments, the control system can adjust the positional velocity (PV) of a treatment device based on a sensed temperature. In some embodiments, the control system can vary power to increase or decrease temperature based on a sensed positional velocity.

Although positional velocity may be obtained and controlled with a positioning device, such as, for example, a servo, positional velocity may also be controlled manually by a user, whereby a suitable indicator such as a display screen may guide the operator in manual adjustment of positional velocity.

Upper and lower thermal injury values can be used as boundaries to promote safety and efficacy during treatment. Upper and lower bounds have been established for Thermal Injury (TI) based on simulation and correlation to clinical experience. The lower bound describes a minimum value of thermal injury capable of effecting an efficacious treatment. The upper bound represents the maximum thermal injury which will be efficacious and still fall within the bounds of safety. Between these bounds, for a selected value of TI, a monotonic value for either control temperature or control positional velocity may be determined. In operation, a value of TI between the upper and lower bounds of safety and efficacy is selected which can be determined by the system or set by the user. After a value of TI has been established, either positional velocity or temperature is set as the control parameter. In some embodiments, the controller can then adjust the positional velocity of the treatment device based on a sensed temperature. In some embodiments, the controller can vary power to increase or decrease temperature based on a sensed positional velocity.

Some of the systems described herein make use of a movable heating device having a generally continuous positional velocity during use. In some other embodiments, a heating device can be stationary, at least temporarily, relative to a treated vessel. Accordingly, in some embodiments, there is no positional velocity during at least a portion of the treatment. A value of TI between the upper and lower bounds of safety and efficacy preferably is selected or predetermined by the system or set by the user. In some embodiments having a stationary device, the control system adjusts the treatment time based on a sensed temperature. In some embodiments having a stationary device, the control system can vary the power to increase or decrease the temperature of the treatment device based on a treatment time that is set by the user. In some embodiments, a long treatment area can be treated by a stationary device that is located in a first position for a sufficient time at an appropriate temperature to treat a first segment of the treatment area. The stationary device is then indexed or moved to a second position for a sufficient time at an appropriate temperature to treat a second segment of the treatment area. Additional segments can be treated in a similar manner.

Thermal Injury (TI) values at the adventitia based on temperature through the vein wall were determined using a numerical finite difference model. This heat transfer model was based on well-known heat transfer equations. Appropriate thermophysical constants were selected to represent tissue properties. The results of this thermal injury modeling produced a matrix of TI values across many temperature and positional velocity conditions, and for the case of a stationary heat source with zero positional velocity, a matrix of TI values across many temperature and time conditions.

Figure 1B:
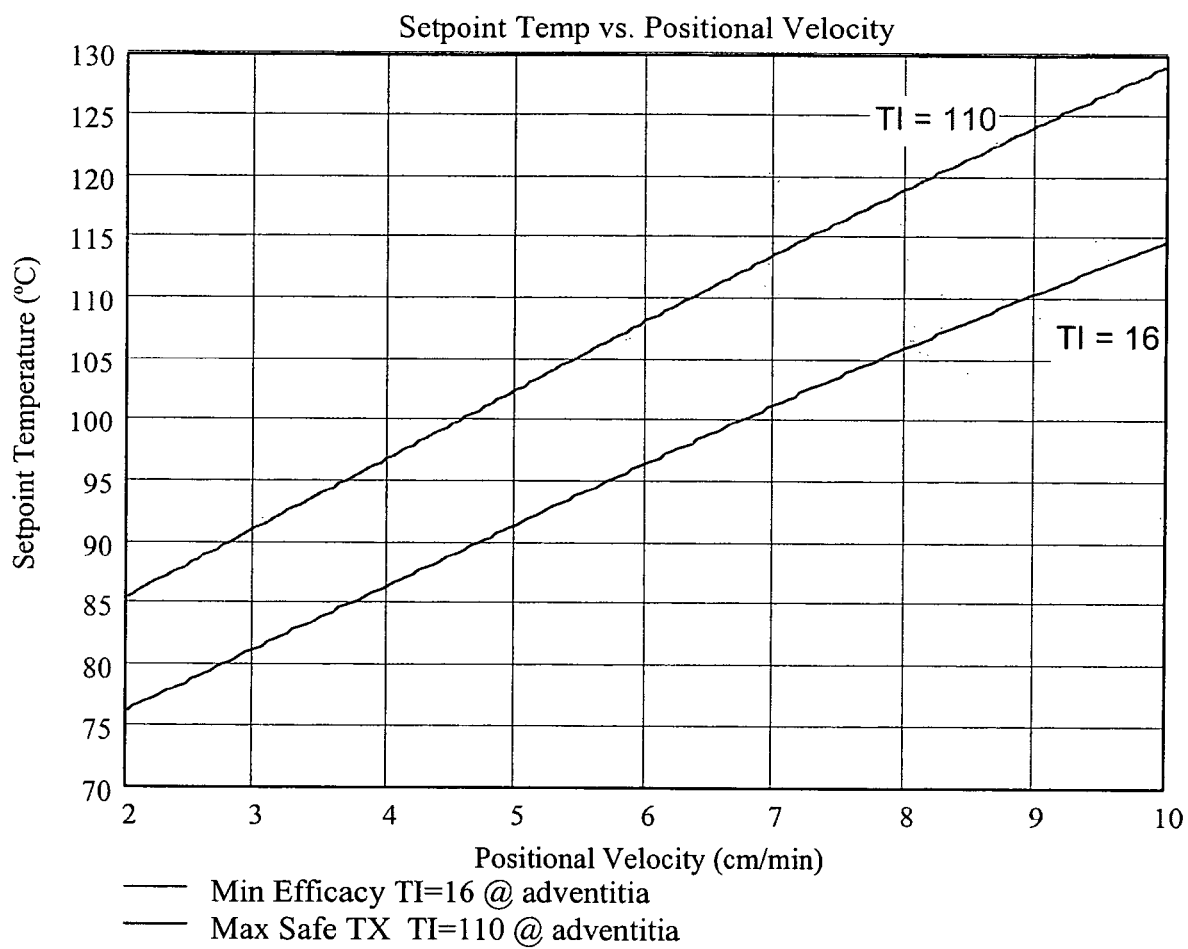
FIG. 1B illustrates a graph of Setpoint Temperature v. Positional Velocity according to one embodiment of a treatment system.
Figure 1C:
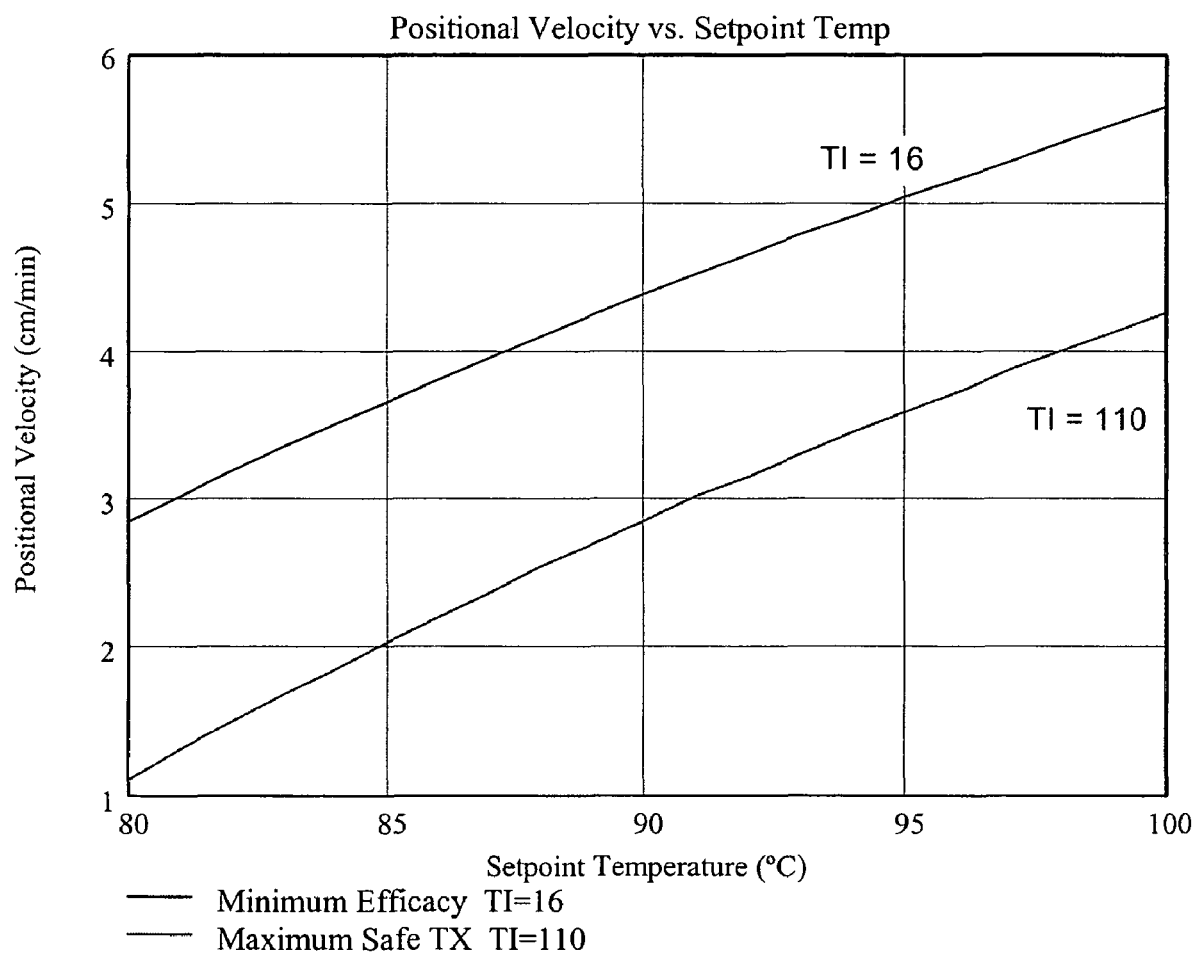
FIG. 1C illustrates a graph of Positional Velocity v. Setpoint Temperature according to one embodiment of a treatment system.

Thermal injury treatment bounds were selected based on clinical experience and examination of calculated adventitial thermal injuries from simulations. For example, as shown in FIGS. 1B and 1C, the lower efficacy bound was determined based on clinical experience at a temperature of 90° C. with a positional velocity of 4.5 cm/min while the upper safety bound was determined based on clinical experience at a temperature of 85° C. with a positional velocity of 2.0 cm/min. Depending on the thermal process rate coefficients for a given tissue, the optimal upper and lower bounds may be calibrated to correspond with the desired clinical outcome. According to one embodiment, the values of 110 and 16 were selected as the upper and lower bounds, respectively, for the case of treating the greater saphenous vein tissue. In some embodiments, the upper and lower bounds can be input input into the controller by the user. In some other embodiments, the upper and lower bounds can be determined or selected by the controller.

The matrix of TI values for ranges of temperature, time and positional velocity were curve fit to create concise expressions, describing data from all the conditions taken at once, for use in a control system. The following relational expressions were derived:

With positional velocity:
T(TI,PV) Controlled temperature is a function of TI and sensed positional velocity.
PV(TI,T) Controlled positional velocity is a function of TI and sensed temperature.

Without positional velocity:
T(TI,t) Controlled temperature is a function of TI and treatment time.
t(TI,T) Treatment time is a function of TI and temperature.

The coefficients for the actual functions describing the control algorithm can be simply constant terms or may be complex functions themselves. Actual equations according to one embodiment are described further below. Additionally, these coefficients may also vary within a range (when a constant) and within the form of an equation (when a function) in order to improve the accuracy of the curve fit to the data. Such variation is within the scope of this invention and may result from selection of the level of accuracy required by and/or designed into the control system.

According to one embodiment, the discrete equations relating temperature, positional velocity and thermal injury are shown below:

$$TI(T,PV) = G_1(T) \cdot e^{G_2(T) \cdot PV}$$

and $$TI(PV,T) = H_1(PV) \cdot e^{H_2(PV) \cdot T}$$

These expressions are further detailed by defining: $G_1(T)$, $G_2(T)$, $H_1(PV)$, and $H_2(PV)$:

$$G_1(T) = \alpha_1 \cdot e^{\beta_1 \cdot T}$$

$$G_2(T) = \alpha_2 \cdot \ln(T) + \beta_2$$

$$H_1(PV) = \alpha_3 \cdot PV^2 + \beta_3 \cdot PV + \kappa_1$$

$$H_2(PV) = \alpha_4 PV^2 + \beta_4 \cdot PV + \kappa_2$$

Where:
TI=Thermal Injury
PV=Positional Velocity (cm/min)
T=Temperature (° C.)
The constants are defined as:

$$\alpha_1 = 2.3 \cdot 10^{-6}, \alpha_2 = 1.3, \alpha_3 = 5.1 \cdot 10^{-8}, \alpha_4 = 3.7 \cdot 10^{-4}$$

$$\beta_1 = 0.24, \beta_2 = 4.6, \beta_3 = -4.5 \cdot 10^{-7}, \beta_4 = -0.014$$

$$\kappa_1 = 3.0 \cdot 10^{-6}, \kappa_2 = 0.23$$

Algebraic manipulation then allows calculation of optimal positional velocity when temperature and thermal injury are defined or selected according to one embodiment. Conversely, the optimal treatment temperature according to one embodiment may be calculated if the positional velocity and temperature are known or selected. The expressions below are provided according to one embodiment:

$$PV(T, TI) = \frac{\ln\left[\frac{TI}{G_1(T)}\right]}{G_2(T)}$$

and $$T(PV, TI) = \frac{\ln\left[\frac{TI}{H_1(PV)}\right]}{H_2(PV)}$$

According to another embodiment, a controller can determine the relationship between setpoint temperature and positional velocity using a chart based on maximum and minimum thermal injury bounds. According to one embodiment, a maximum thermal injury bound at the adventitia is 110, representing the upper bound for a safe treatment. A minimum thermal injury bound at the adventitia is 16, representing the lower bound for an efficacious treatment. Accordingly, in one embodiment, the controller determines an appropriate relationship between temperature and positional velocity by referencing a look-up table, such as, for example, the look-up table shown below. The controller can then provide an output to adjust temperature or positional velocity to control the effectiveness of the treatment.

| Temperature (° C.) | Positional Velocity (cm/min) |
|---|---|
| 80 | 1-2.25 |
| 85 | 2-3.6 |
| 90 | 2.75-4.5 |
| 95 | 3.6-5.6 |
| 100 | 4.3-6.7 |

The relationship for Temperature Setpoint vs. Positional Velocity according to one embodiment is shown graphically in FIG. 1B. Similarly, the relationship for Positional Velocity vs. Temperature Setpoint is shown graphically in FIG. 1C.

Although numerical expressions for the case without positional velocity are not presented, a reasonable set of equations can be formulated in similar fashion to those presented above in the example with positional velocity. However, result tables and graphs for these relationships are shown below. The table below shows tissue heating times for a given temperature without positional velocity based on the same upper and lower bounds used for thermal injury as in the previously described case with positional velocity. Accordingly, in one embodiment, the controller determines an appropriate relationship between temperature and time by referencing a look-up table, such as, for example, the look-up table shown below. The controller can then provide an output to adjust temperature or time to control the effectiveness of the treatment.

| Temperature (° C.) | Time (sec) |
|---|---|
| 80 | 4.8-8.3 |
| 85 | 3.7-6.0 |
| 90 | 3.0-4.6 |
| 95 | 2.5-3.6 |
| 100 | 2.0-3.1 |

Figure 1D:
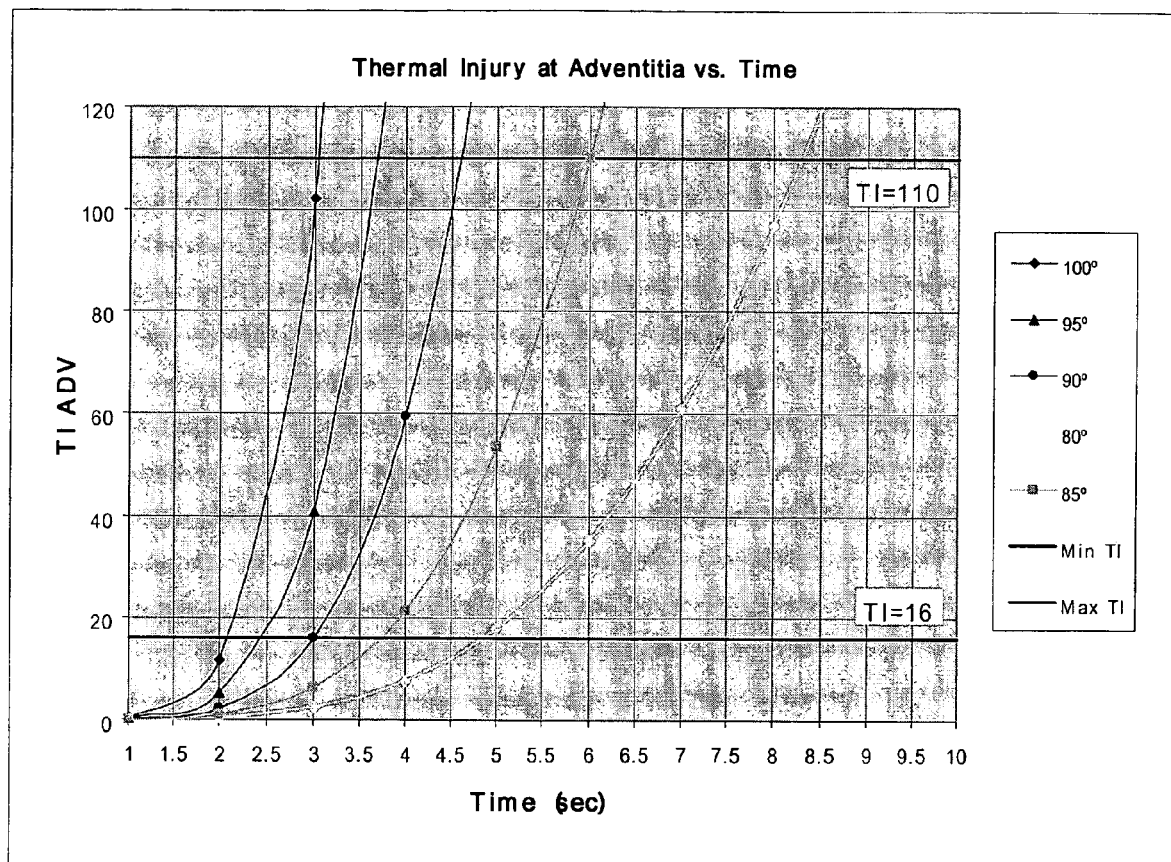
FIG. 1D illustrates a graph of Thermal Injury at Adventitia v. Time according to one embodiment of a treatment system.

The relationship for Thermal Injury at Adventitia vs. Time according to one embodiment is shown graphically in FIG. 1D. As stated above, thermal injury is highly dependent on the selection of the thermal process rate coefficients for a given tissue, A and Ea, which are used in the Arrhenius thermal injury calculation. These coefficients are dependant on the type of tissue being heated and may be obtained either from published literature or may require experimental determination using such techniques as Digital Scanning Calorimetry. According to some embodiments, the system comprises a Digital Scanning Calorimeter, or other suitable device, for determining the thermal process rate coefficients for a given tissue. In some other embodiments, the controller is programmed with a look-up table having known thermal process rate coefficients for tissues upon which the treatment system is to be used. As such, control algorithm predictions may vary within a range with accuracy of prediction dependent on the exactness of the selected thermal process rate coefficients used by the control algorithm to the native tissue's actual thermal process rate coefficients.

Where expanding electrodes are employed to impart radiofrequency energy to the vein wall, as will be described further below, the electrode apposition force affects the delivery of electrical energy. This force causes the electrode to make intimate contact with the vessel intima and it ensures low contact-resistance of the electrodes with the vessel intima preferably resulting in an efficient and consistent transmission of radiofrequency energy to the vessel. An insufficient force may allow blood to collect and coagulate around the electrodes and would reduce the effective vessel-contact surface area. As a result, the device performance could diminish because of the increased resistance between the electrode surface and the vessel. In some cases, sufficiently coagulated blood could cause total loss of contact between the electrode and the vessel. One advantage of the feedback control system is to commensurately reduce overall power delivered to tissue based on bio-informatic information. Conversely, excessive apposition force could prevent the electrodes from collapsing under the loads imparted by the vessel shrinkage which is effected by collagen denaturation and contraction and, as a result, prevent effective occlusion. An effective electrode apposition force can be applied to the treated vessel.

A cantilever radial electrode design provides electrodes that automatically adjust in both radial and circumferential spacing. This adjusting configuration provides the benefit of increased volumetric heating capacity as the electrodes are collapsed radially inward. That is, as the inter-electrode distance and the arc-distance between polarities are reduced, the resistance declines. As a result, more radiofrequency current may be directed into the surface area causing increased heating in the volume of tissue subtended by the electrode poles.

An external compressive load created by perivenous tumescent infiltration, manual compression, and/or tourniquet wrapping provides additional support for durable molding and occlusion of the vessel. Placing the vein under a radially-compressive load, delivering sufficient thermal energy to cause irreversible denaturation of the collagen, and subsequently allowing the vessel to cool while in this compressed state will cause the vessel to be durably molded in an occluded state. In addition, this same radially compressive load imparts strain on the collagen fibril bundles which reduces the collagen denaturation temperature, and thereby promotes faster transfiguration.

Water plays a role in governing collagenous tissue properties. In fact, collagen denaturation increases with increased hydration at a given temperature. For example, the thermal stability of collagen decreases with increased tissue hydration or increased ionic composition in the bathing solution. Renaturation of the tissue (which may happen, in part, regardless of the magnitude of injury) is greater if the tissue is maintained under load because the load tends to organize the structure and promote reformation of some of the triple-helix structures of collagen. This renaturation effect happens on the order of hours following heating and the restoration to normal body temperature. In some cases, complete vessel shrinkage may not be achieved where a vessel wall is poorly hydrated. In the case of a catheter pullback treatment technique, the level of vessel wall hydration can be decreased by not having an adequate fluid (e.g., saline) drip or where the fluid is running off too quickly. Preferably, a load is applied to maintain compression on the vessel during the procedure as well as post-procedurally. The compression load applied during the procedure and over the days following the procedure help to "mold" the vessel "closed" as some of the collagen undergoes renaturation. Good collagen denaturation and consequent vessel shrinkage can be achieved where cuff compression or well-placed external compression is applied to the vein.

The relatively cool perivascular tumescent fluid provides faster cooling of the heated vessel, which additionally promotes the durable molding to its compressed and shrunken state. The described treatment methods are preferably accomplished in a near-bloodless field. The vessel may be exsanguinated through various means: Trendelenburg positioning, perivascular tumescent infiltration, tourniquet wrapping, and/or manual compression.

Additionally, a fluid drip of saline into the target vessel can reduce the potential for platelet aggregation by creating a bloodless field and a more conductive environment. Also, denaturation of collagen increases with hydration. The tumescent on the adventitia and the saline in the lumen help to better hydrate the tissue to be treated. Additionally, in some embodiments, a layer of perivascular fluid (e.g., saline, gas, gel, tumescence, etc.) acts as a heat sink to provide protection to surrounding tissue.

Further, apparatuses including balloons, umbrellas, plugs, etc. can be used as exsanguinations methods to perform the described treatment in a flow condition. In one embodiment, the infusion of saline is an aspect of the treatment. The infusion drip rate may be controlled as a function of dwell time and/or positional velocity. As the treatment device is withdrawn along a treatment length, the saline drip is intended to displace (exsanguinate) residual or inflowing blood. If the withdrawal rate is increased, a greater amount of saline should be used. For example, a 6 mm vessel can be treated over a length of 3 cm in 1 minute. The volume of the treated space is 0.85 cc. The minimum effective drip rate preferably is about 1.5 times the volume of the treated space over the treatment time, or about 1.27 cc/minute. Larger vessels and/or faster withdrawal rates may necessitate a faster drip rate. The above change-rate relationship allows for effective exsanguination.

The location of the infusion drip can also have bearing on the effectiveness of exsanguination. For example, the drip could be situated at the distal tip of the treatment device, infused through the sheath just proximal of the electrodes, or through side-ports just below the electrodes, or through a vessel access port used remotely from the starting treatment site.

In some embodiments, the coined, spherical electrodes have greater effectiveness than simply flat electrodes. In addition, their low mass allows the electrodes and, as a result, the vessel to cool quickly. Therefore, the targeted vessel temperature is achieved quickly following the application of RF energy.

Except as described herein, the systems, devices, methods and techniques described herein may, in some embodiments, be similar to any one or more of the systems, devices, methods and techniques described in U.S. Pat. Nos. 6,401,719; 6,258,084; 6,237,606; 6,200,312; and 6,179,832. In addition, the systems, devices, methods and techniques described herein may, in certain embodiments, be applied to or used in connection with any one or more of the systems, devices, methods and techniques disclosed in the above-mentioned U.S. Pat. Nos. 6,401,719; 6,258,084; 6,237,606; 6,200,312; and 6,179,832. The above-mentioned U.S. Pat. Nos. 6,401,719; 6,258,084; 6,237,606; 6,200,312; and 6,179,832 are hereby incorporated by reference herein and made a part of this specification.

Figure 2:
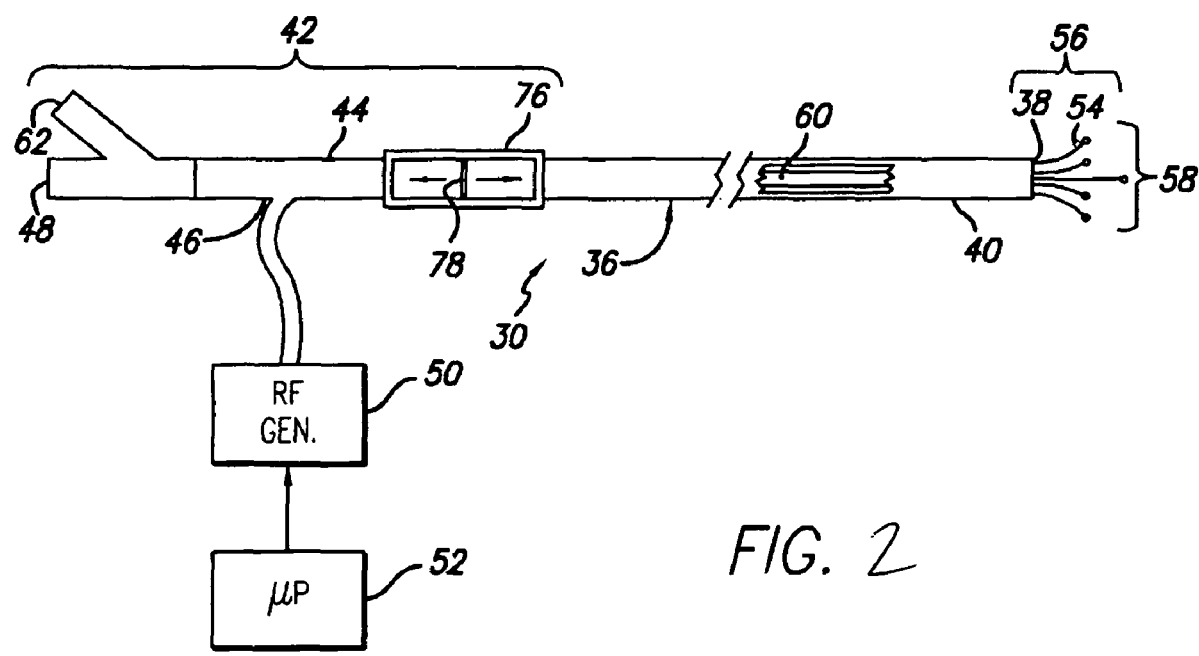
FIG. 2 illustrates an energy application system that may be used in conjunction with one method of the present invention, depicting a partial cutaway view of the first embodiment of the catheter showing both the working end and the connecting end with an RF generator and a microprocessor connected at the connection end.

Some additional features and advantages of some embodiments are now described with respect to FIGS. 2-16D. One preferred embodiment of a catheter for delivering an expandable energy application device or expandable electrode device 56 to the venous treatment site is illustrated in FIG. 2. The catheter 30 includes an expandable energy application device 56 which in this embodiment, comprises an array of electrodes 58, an outer sheath 36 having a distal orifice 38 at its working end 40. The connector end 42 of the outer sheath is attached to a handle 44 that includes electrical connector 46. The handle additionally includes a guide wire port 48. The connector 46 is for interfacing with a power source, such as, for example, an RF generator 50, and a microprocessor controller 52. The power source and microprocessor controller can be contained in one unit in some embodiments. The microprocessor controller preferably controls the treatment device as described in one or more of the embodiments described above. For example, the controller 52 can sense an input control parameter and can output a resultant control parameter to effectuate treatment. For example, the controller can control the position of the catheter in response to external commands and data from a temperature sensor 54, such as a thermocouple, or temperature sensors that may be positioned at an intraluminal venous treatment site.

The catheter 30 includes the expandable electrode device 56 that moves in and out of the outer sheath by way of the distal orifice 38 in this embodiment, although in other embodiments the device 56 may expand from and contract into the catheter 30 at other locations. The expandable electrode device 56 includes a plurality of electrodes 58 which can be expanded by moving the outer sheath 36 relative to the electrodes. Although FIG. 2 illustrates a plurality of electrodes 58 surrounding a single central electrode, different electrode configurations may be used.

Contained within the outer sheath 36 is an inner sheath 60 or inner member as shown in the cutaway portion of FIG. 2. A fluid port 62 communicates with the interior of the outer sheath. The catheter 30 can be periodically flushed out with saline through the fluid port. The flushing fluid can travel between the outer sheath and the inner sheath. The fluid port also allows for the delivery of drug therapies or other fluids during treatment. Flushing out the catheter prevents the buildup of biological fluid, such as blood, within the catheter. The treatment area or site of the vein can be flushed with a fluid such as saline, or a high impedance dielectric fluid, in order to evacuate blood from the treatment area of the vein so as to prevent the formation of coagulum or thrombosis. The use of a high impedance dielectric fluid can minimize unintended heating effects away from the treatment area. The dielectric fluid directs the current of RF energy toward the vein wall. In addition, a vasoconstrictive agent may be applied to shrink the vein, heparin may be applied for coagulation avoidance, and a sclerosing agent may be applied to assist in ligation. These drugs or agents may be applied before, during, or after the catheter is used to heat the vein wall.

In one preferred embodiment, the catheter 30 includes a lumen which begins at the distal tip 55, proximate the working end 40, and runs substantially along the axis of the inner member before terminating at the guide wire port 48 of the handle 44. A guide wire can be introduced through the lumen of the catheter for use in guiding the catheter to the desired treatment site. Where the catheter is sized to treat smaller veins, the outer diameter of the catheter may not allow for a fluid flush between the outer sheath and the inner sheath 60. However, a fluid flush can be introduced through the guide wire port 48 in such an embodiment.

Turning again to FIG. 2, an actuator 76 controls the extension of the electrode device 56 through the distal orifice 38. The actuator may take the form of a switch, lever 78, threaded control knob, or other suitable mechanism, and is preferably one that can provide fine control over the movement of the outer sheath 36 or the inner sheath 60, as the case may be. In one embodiment of the invention, the actuator interfaces with the outer sheath to move it back and forth relative to the inner sheath. In another embodiment the actuator interfaces with the inner sheath to move it back and forth relative to the outer sheath. The relative position between the outer sheath and inner sheath is thus controlled, but other control approaches may be used. In some embodiments, the controller can control the relative position of the outer and inner sheaths in response to one or more control parameters or input commands.

One preferred embodiment of a catheter 90 is illustrated in FIG. 3. An inner member 92 or sheath is contained within the outer sheath 94. The inner sheath is preferably constructed from a flexible polymer such as polymide, polyethylene, or nylon, and can travel the entire length of the catheter. The majority of the catheter can be flexible so as to navigate the tortuous paths of the venous system. A hypotube having a flared distal end 98 and a circular cross-sectional shape is attached over the distal end of the inner sheath 92. The hypotube 96 is preferably no more than about two to three centimeters in length. The hypotube acts as part of a conductive secondary lead 100. An uninsulated conductive electrode sphere 102 is slipped over the hypotube. The flared distal end of the hypotube prevents the electrode sphere from moving beyond the distal end of the hypotube. The sphere is permanently affixed to the hypotube, such as by soldering the sphere both front and back on the hypotube. The majority of the surface of the electrode sphere remains uninsulated. The remainder of the hypotube is preferably insulated so that the sphere-shaped distal end can act as the electrode. For example, the hypotube can be covered with an insulating material such as a coating of parylene. The interior lumen of the hypotube is lined by the inner sheath 92 which is attached to the flared distal end of the hypotube by adhesive such as epoxy.

Surrounding the secondary lead 100 are a plurality of primary leads 104 that preferably have a flat rectangular strip shape and can act as arms. In one configuration, the strip shape is a width from 0.76 mm (0.03 in) to 1.00 mm (0.04 in) and a thickness of approximately 0.13 mm (0.005 in.). As illustrated in FIG. 5, the plurality of primary leads 104 is preferably connected to common conductive rings 106. This configuration maintains the position of the plurality of primary leads, while reducing the number of internal electrical connections. The conductive rings 106 are attached to the inner sheath 92. The position of the rings and the primary leads relative to the outer sheath 94 follows that of the inner sheath. As earlier described, the hypotube 96 of the secondary lead is also attached to the inner sheath. Two separate conductive rings can be used so that the polarity of different primary leads can be controlled separately. For example, adjacent primary leads can be connected to one of the two separate conductive rings so that the adjacent leads can be switched to have either opposite polarities or the same polarity. The rings are preferably spaced closely together, but remain electrically isolated from each other along the inner sheath. Both the rings and the hypotube are coupled with the inner sheath, and the primary leads that are connected to the rings move together with the secondary lead while remaining electrically isolated from the secondary lead. Epoxy or another suitable adhesive can be used to attach the rings to the inner sheath. The primary leads from the respective rings alternate with each other along the circumference of the inner sheath. The insulation along the underside of the leads prevents an electrical short between the rings. FIG. 4 illustrates an end view of the working end of catheter 90 taken along line 6-6 of FIG. 5.

The conductive rings 106 and the primary leads 104 are attached together to act as cantilevers where the ring forms the base and the rectangular primary leads operate as the cantilever arms. The primary leads are formed to have an arc or bend such that the primary leads act as arms that tend to spring outwardly away from the catheter 90 and toward the surrounding venous tissue. Insulation along the underside of the primary leads and the conductive rings prevents unintended electrical coupling therebetween. Alternately, the primary leads are formed straight and connected to the conductive rings at an angle such that the primary leads tend to expand or spring radially outward from the conductive rings. The angle at which the primary leads are attached to the conductive rings should be sufficient to force the primary distal ends and their electrodes 108 through blood and into apposition with the vein wall 80 but not enough to preclude vein shrinkage. In particular, the primary leads 104 are formed with enough strength, and are mounted or bent such that they expand outwardly into apposition with the inner wall of the vein. However, the force they develop in an outward direction is not strong enough to prevent radial shrinkage of the vein. As the vein shrinks, due to the heating caused by the energy delivered by the electrodes 108, the shrinking vein causes a contraction of the primary electrodes. Due to the outward force constantly exerted by the primary leads 104, the electrodes 108 remain in constant apposition with the vein wall as it shrinks.

Other properties of the primary leads, such as lead shape and insulation thickness, affect the push force of the lead against the vein wall and the degree of arc or bend can be adjusted to compensate for these factors. The rectangular cross section of the primary leads can provide increased stability in the lateral direction while allowing the necessary bending in the radial direction. The primary leads are less likely to bend sideways when expanded outward due to the increased size of the rectangular lead in that sideways direction, and a uniform spacing between primary leads is more assured. Uniform spacing between the primary leads and the distal ends promotes uniform heating around the vein by the electrodes 108.

The distal ends of the primary leads 104 are uninsulated to act as the electrodes 108 having a rounded shape. In the embodiment shown, the shape is convex which may take the form of a spoon or hemispherical shape. The primary leads can be stamped to produce an integral shaped electrode at the distal end of the primary leads. The uninsulated outer portion of the distal end of the electrodes 108 which are to come into apposition with the wall of the vein is preferably rounded and convex. The flattened or non-convex inner portion of the distal end is insulated to minimize any unintended thermal effect, such as on the surrounding blood in a vein. The distal ends of the electrodes 108 are configured such that when the distal ends are forced toward the inner sheath 92, as shown in FIG. 4 the distal ends combine to form a substantially spherical shape with a profile smaller than the spherical electrode 102 at the secondary distal end.

In one preferred embodiment as shown in FIG. 5, the electrodes 108 comprise a convex, square center section with semi-circular ends. It has been found that this "race track" configuration maximizes surface area of contact for the electrodes 108 shown.

The outer sheath 94 can slide over and surround the primary and secondary leads 100 and 104. The outer sheath includes an orifice 110 which is dimensioned to have approximately the same size as the spherical electrode 102 at the secondary distal end. A close or snug fit between the spherical electrode 102 and the orifice 110 of the outer sheath preferably is achieved. This configuration provides an atraumatic tip for the catheter 90. The spherical electrode 102 is preferably slightly larger than the orifice 110. The inner diameter of the outer sheath is approximately the same as the diameter of the reduced profile of the combined primary distal end electrodes 108.

A fluid port (not shown) can communicate with the interior of the outer sheath 94 so that fluid can be flushed between the outer sheath and inner sheath 92 as described above. Alternately, a fluid port can communicate with a central lumen 112 in the hypotube which can also accept a guide wire for use in guiding the catheter to the desired treatment site. It is to be understood that another lumen can be formed in the catheter to deliver fluid to the treatment site. The delivered fluid displaces or exsanguinates blood from the vein so as to avoid heating and coagulation of blood. The delivery of a dielectric fluid increases the surrounding impedance so that RF energy is directed into the tissue of the vein wall. An alternate fluid could be a sclerosing agent which could serve to displace blood or to further enhance occlusion of the vein when applied before, during, or after energy delivery. The fluid can also include an anticoagulant such as heparin which can chemically discourage the coagulation of blood at the treatment site. The catheter 90 can be periodically flushed with saline which can prevent the buildup of biological fluid, such as blood, within the catheter. The saline can be flushed through the central lumen 112 or between the inner and outer sheaths. If a central lumen is not desired, the lumen of the hypotube can be filled with solder.

The electrode device 114 can operate in either a bipolar or a monopolar configuration. When adjacent primary leads have opposite polarity, a bipolar electrode operation is available. When the primary leads are commonly charged a monopolar electrode operation is available in combination with a large return electrode pad placed in contact with the patient. When the primary electrodes 108 are commonly charged or have a first potential, and a secondary electrode 102 has an opposite polarity or different potential, a bipolar electrode operation is available. More or fewer leads may be used. The number of leads can be dependent on the size or diameter of the vein to be treated, as described above.

Although not shown, it is to be understood that the catheter 90 can include one or more of the sensors mentioned above. For example, catheter 90 can include temperature sensors, such as thermocouples, mounted in place on an electrode 108 so that the sensor is substantially flush with the exposed surface of the electrode 108. (The sensor is shown in a raised position in the drawings for clarity of illustration only). The temperature sensor senses the temperature of the portion of the vein that is in apposition with the exposed electrode 108 surface. Application of RF energy from the electrodes 108 is halted or reduced when the monitored temperature reaches or exceeds the specific temperature that was selected by the operator or controller, such as the temperature at which venous tissue begins to cauterize. In some embodiments, a control parameter of the catheter can be controlled by the controller in response to another sensed control parameter. Other techniques such as impedance monitoring and ultrasonic pulse echoing can be sensed by the controller in an automated system to determine a control parameter, such as positional velocity or dwell time. The control system can adjust the application of RF energy from the electrodes to the venous section to achieve sufficient shrinkage of the vein 22 based on sensed parameters. The controller can also help avoid overheating of the vein.

Figure 7:
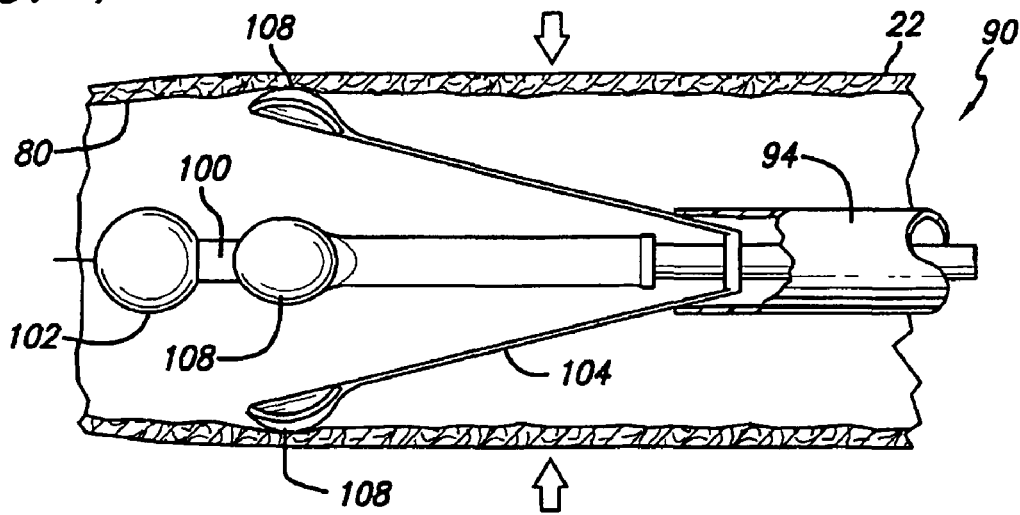
FIG. 7 illustrates a cross-sectional view of a vein after the vein has been compressed, although not to full occlusion, by tumescent anesthesia fluid, the vein containing the catheter of FIG. 3 with the electrodes in apposition with the vein.
Figure 8:
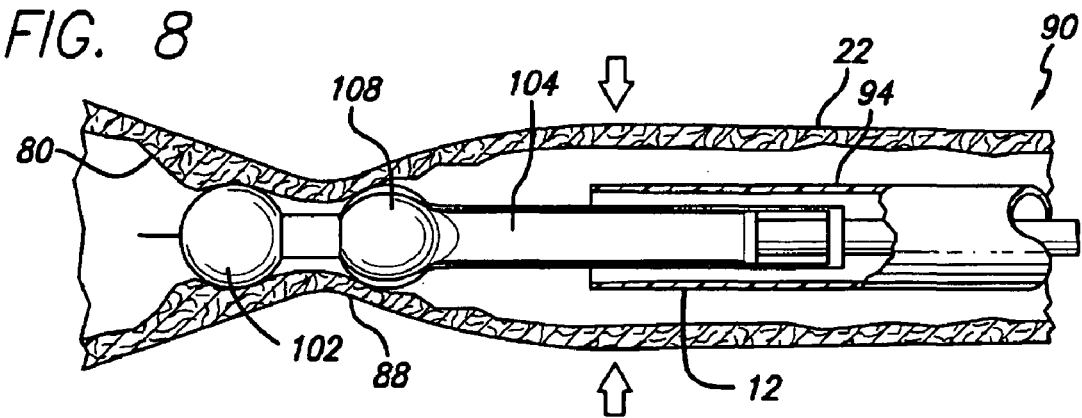
FIG. 8 illustrates a cross-sectional view of the compressed vein containing the catheter of FIG. 3 where the vein is being ligated by the application of energy from the electrodes.

Referring now to FIGS. 7 and 8, in the operation of this embodiment of a catheter 90, the catheter is inserted into a vein 22. Fluoroscopy, ultrasound, an angioscope imaging technique, or another technique may be used to direct and confirm the specific placement of the catheter in the vein. In some embodiments, a fluoroscopic, ultrasound, and or angioscope imaging device can be in communication with the controller to sense and control the application of the treatment device. Impedance measurements can also be used to determine proper positioning of the catheter, particularly at the ostium of a vessel such as at the sapheno-femoral junction. Impedance measuring devices can be coupled with and/or in communication with the controller. The impedance will be low when the electrodes are in the blood stream. The catheter can then be moved until a high impedance value is obtained, indicating electrode contact with the vein wall. The vein wall 80 has been compressed by the introduction of tumescent anesthesia into the tissue surrounding the vein as indicated by the arrows. The arrows in the figures indicate the compression of the tissue. Unless stated otherwise, all drawing figures having arrows indicating tissue compression are not drawn to scale for purposes of clarity of illustration and are meant to be representations of the vein in a nearly fully occluded state.

The reduction in the vein 22 diameter caused by the tumescence of the tissue in contact with the treatment site assists in pre-shaping the vein to be molded to a ligated state. The compression also exsanguinates the vein and forces blood away from the treatment site, thus preventing coagulation.

The actuator 76 (FIG. 2) is then operated to retract the outer sheath 94 to expose leads the 100 and 104. As the outer sheath no longer restrains the leads, the primary leads 104 move outward relative to the axis defined by the outer sheath, while the secondary lead 100 remains substantially linear along the axis defined by the outer sheath. The primary leads continue to move outward until their electrodes 108 are placed in apposition with the vein wall 80 and the outward movement of the primary leads is impeded. The primary electrodes 108 contact the vein wall along a generally circumferential area or band of the vein wall. This outward movement of the primary leads occurs in a substantially symmetrical fashion so that the primary electrodes 108 are substantially evenly spaced. Alternately, the electrodes 86 can be spaced apart in a staggered fashion such that they do not lie in the same plane. For example, the adjacent electrodes 86 can extend different lengths from the catheter so that a smaller cross-sectional profile is achieved when the electrodes 86 are collapsed toward one another.

When the electrodes 102 and 108 are positioned at the treatment site of the vein, the RF generator 50 is activated to provide suitable RF energy. One suitable frequency is 510 kHz. One criterion used in selecting the frequency of the energy to be applied is the control desired over the spread, including the depth, of the thermal effect in the venous tissue. Another criterion is compatibility with filter circuits for eliminating RF noise from thermocouple signals. In a bipolar operation, the primary electrodes 108 are charged with one polarity opposite that of the secondary electrode 102. The coupling between oppositely charged primary and secondary electrodes produces RF fields therebetween, and form a symmetrical RF field pattern along a circumferential band of the vein wall 80 to achieve a uniform temperature distribution along the vein wall being treated.

The RF energy produces a thermal effect which causes the venous tissue to shrink, reducing the diameter of the vein 22. The thermal effect produces structural transfiguration of the collagen fibrils in the vein. The collagen fibrils shorten and thicken in cross-section in response to the heat from the thermal effect. As shown in FIG. 8, the energy causes the vein wall 88 to collapse until further collapse is impeded by the primary lead electrodes 108. The primary lead electrodes are pressed closer together by the shrinking vein wall and assume a reduced profile shape which is sufficiently small so that the vein is effectively ligated.

Figure 9:
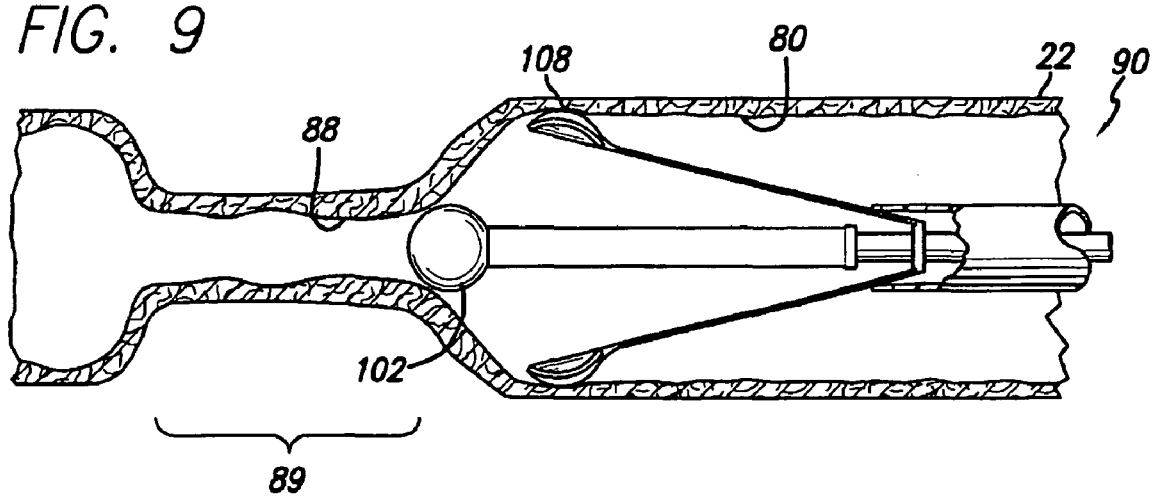
FIG. 9 illustrates a partial cross-sectional view of the vein wall of FIG. 8 showing a lengthy effective occlusion made by moving the electrodes along the treatment site of the vein while maintaining the electrodes in apposition and continuing to apply energy to the vein wall.

The catheter 90 is pulled back while continuing energy delivery as shown in FIG. 9. In some embodiments, the positional velocity of the catheter is controlled by the controller actuating a positioning device, such as, for example, a servo device. In some other embodiments, the target positional velocity can be displayed with the actual positional velocity to facilitate the user pulling back on the catheter at the desired speed. In other embodiments, the positional velocity is sensed by the controller and the temperature or power delivered to the catheter is adjusted by the controller based on the pullback speed. Ligation as the catheter is being retracted produces a lengthy occlusion 89 which is stronger and less susceptible to recanalization than an acute point occlusion.

In a monopolar operation, the secondary-lead electrode 102 remains neutral, while the primary electrodes 108 are commonly charged and act in conjunction with an independent electrical device, such as a large low-impedance return pad (not shown) placed in external contact with the body, to form RF fields substantially evenly spaced around the circumference of the vein. The thermal effect produced by those RF fields along the axial length of the vein wall 80 causes the vein wall to collapse around the primary lead electrodes. The electrode device is retracted as described in the bipolar operation.

In either bipolar or monopolar operation the application of RF energy is substantially symmetrically distributed through the vein wall, as previously described. The electrodes preferably are spaced less than about 4 or 5 millimeters apart along the circumference of the vein wall 80, which defines the target vein diameter for a designed electrode catheter. Where the electrodes are substantially evenly spaced in a substantially symmetrical arrangement, and the spacing between the electrodes is maintained, a symmetrical distribution of RF energy increases the predictability and uniformity of the shrinkage and the strength of the occlusion.

Although not shown, in another embodiment, the primary leads may be mounted or otherwise configured such that they expand outwardly in an asymmetrical fashion. One purpose for an asymmetrical electrode arrangement is to only shrink a portion of the vein wall to achieve occlusion. Such may be desired in the case of preferentially shrinking a tributary branch or aneurysm on one side of the vein.

After completing the procedure for a selected venous section or treatment site, the actuator 76 causes the primary leads 104 to return to the interior of the outer sheath 94. Once the primary leads are within the outer sheath, the catheter 90 may be moved to another venous section where the ligation process is repeated.

Figure 10:
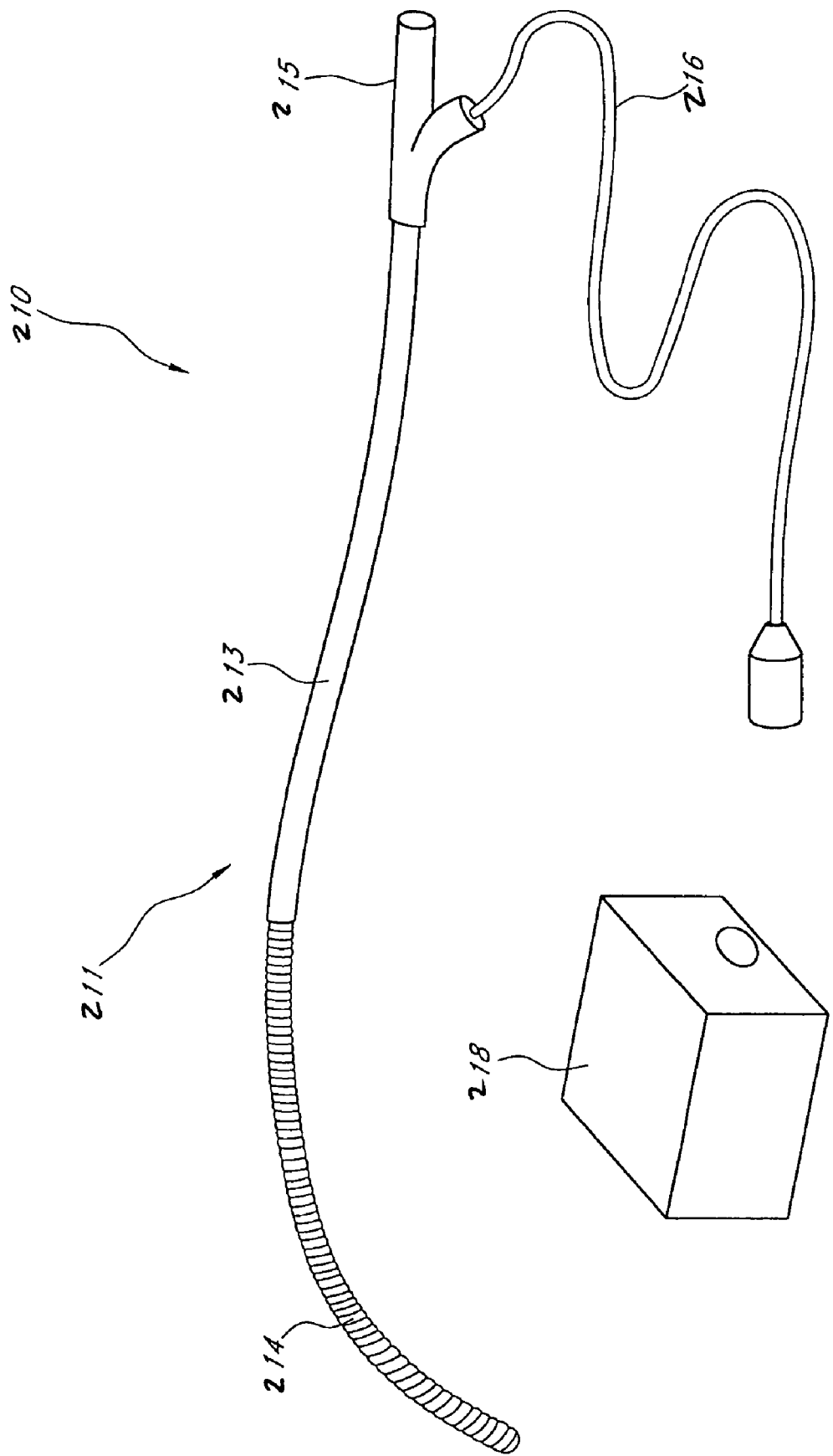
FIG. 10 illustrates an overall view of a resistive element system usable to treat a hollow anatomical structure, according to an embodiment of the invention.

FIG. 10 illustrates another embodiment of a treatment system 210 for applying energy to a HAS. As illustrated, the treatment system 210 comprises a catheter 211. The catheter 211 includes a catheter shaft 213, which may be used to maneuver a distal portion 214 of the catheter 211 during placement. In certain embodiments, the catheter shaft 213 comprises a biocompatible material having a low coefficient of friction. For example, the shaft 213 may comprise a polyimide. In other embodiments, the shaft 213 may comprise PEEK, TEFLON®, HYTREL®, or any other such suitable material.

In certain embodiments, the catheter shaft 213 is sized to fit within a vascular structure that may be between approximately two and approximately fourteen French in diameter and preferably between approximately four French and approximately eight French, which corresponds to a diameter of between approximately 1.3 millimeters (0.05 inch) and approximately 2.7 millimeters (0.10 inch). In still other embodiments, other sizes of catheters may be used. In certain embodiments, the distal portion 214 transfers energy (e.g., heat) directly to an inner wall of a HAS. The proximal end of the catheter has a handle 215. The handle 215 can include a port for fluid and a connection 216 for interfacing with an energy source 218.

In certain embodiments, the energy source 218 comprises an alternating current (AC) source, such as an RF generator. In other embodiments, the energy source 218 comprises a direct current (DC) power supply, such as, for example, a battery, a capacitor, or other energy source. The energy source 218 may also incorporate a controller. In some other embodiments, a controller is provided separate from the energy source.

A controller (e.g., the controller 10 of FIG. 1A) can comprise a processor. Through the use of a processor, the controller can receive input signals from the user or from sensors, and can send output signals to facilitate the control of the therapeutic element as described above. For example, the controller can adjust the positional velocity based upon readings from a temperature sensor (e.g., a thermocouple or a resistance temperature device) located in the working portion (e.g., therapeutic portion) of the catheter 211. In another embodiment, the controller may adjust the temperature or power delivered to the working portion of the catheter in response to the positional velocity and/or dwell time of the catheter. In an alternative embodiment, the user can select a constant temperature and/or power output of the energy source 218 and the positional velocity and/or dwell time of the catheter will be adjusted. In another embodiment, the flow rate of a liquid delivered by the catheter can be sensed and/or adjusted based on other control parameters as described above. In another embodiment, a user can input TI values to the controller. In another embodiment, a user can input data to the controller, and the controller can calculate or otherwise determine the TI values. In some embodiments, the controller determines the TI values based on sensed parameters.

Figure 11:
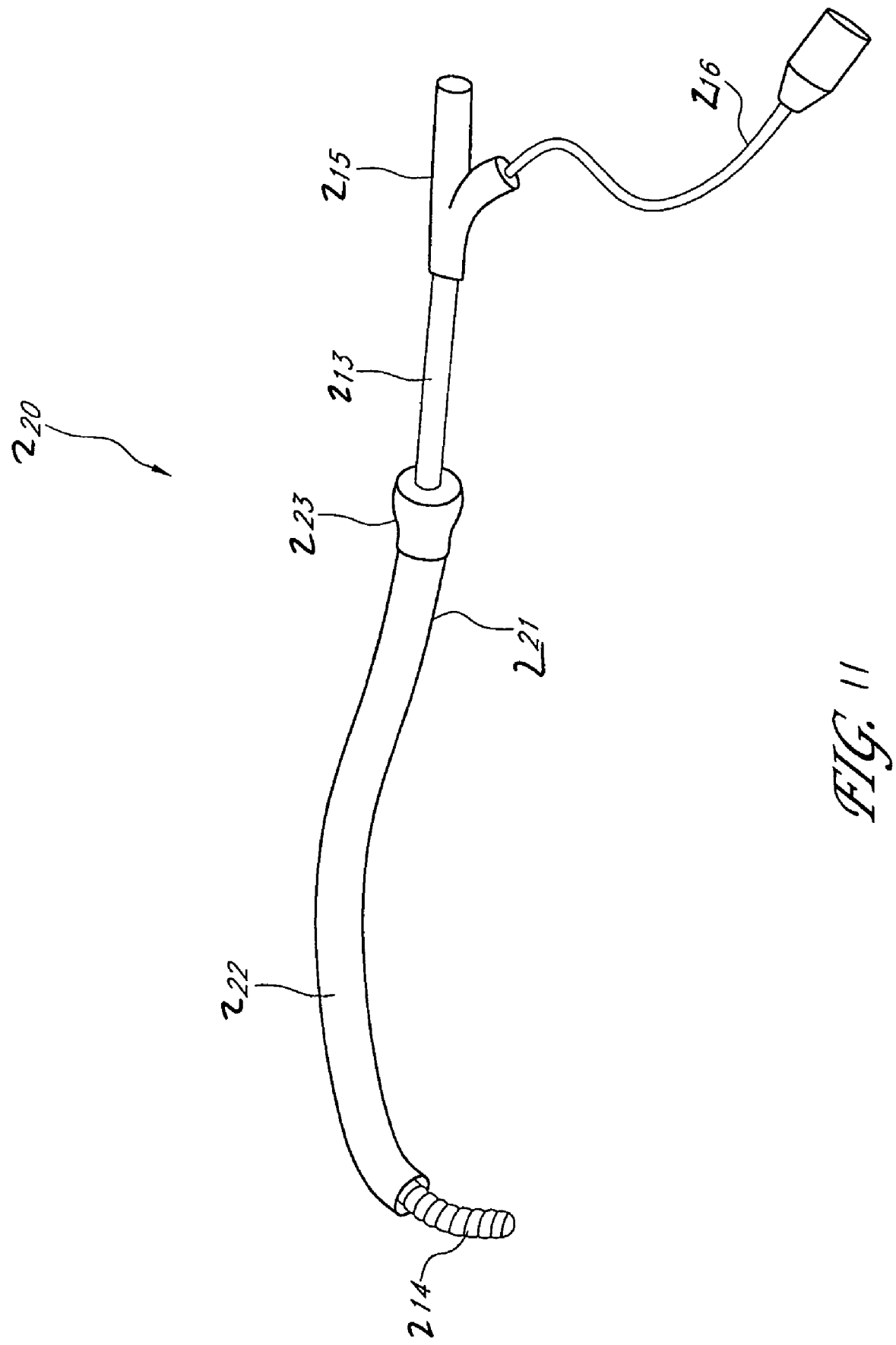
FIG. 11 illustrates an exemplary embodiment of a catheter sheath in a partially retracted position usable with the resistive element system of FIG. 10.

FIG. 11 illustrates another embodiment of a resistive element system 220. As shown, a catheter 221 includes an outer retractable sheath 222. The sheath 222 is advantageously used to protect the device during placement, facilitate introduction of the device, and/or adjust the exposed axial length of the resistive element 214 (i.e., therapeutic element) for a user-selected and/or variable treatment length. For example, the sheath 222 may be used (e.g., pulled back (proximally) or pushed forward (distally)) to adjust the length of the heated region of the resistive element 214 that is exposed to a wall of the HAS. In some embodiments the relative positioning of the sheath can be adjusted by a controller of the treatment system.

FIG. 11 further shows an optional sensor 223 coupled to the sheath 222 and the shaft 213. In other embodiments, multiple sensors are placed along the axial resistive element length. For example, the controller and/or energy source may advantageously monitor the individual sensors and use data received therefrom for feedback to control one or more treatment parameters. In another embodiment, a controller may monitor for high temperature or low temperature signals. For example, an algorithmic process may be used to control the current applied to the various wire coils, thus maintaining a substantially axially-uniform temperature and/or heat output. In some embodiments, positional velocity can be sensed by a positioning device and the temperature can be adjusted by the controller.

Figure 12:
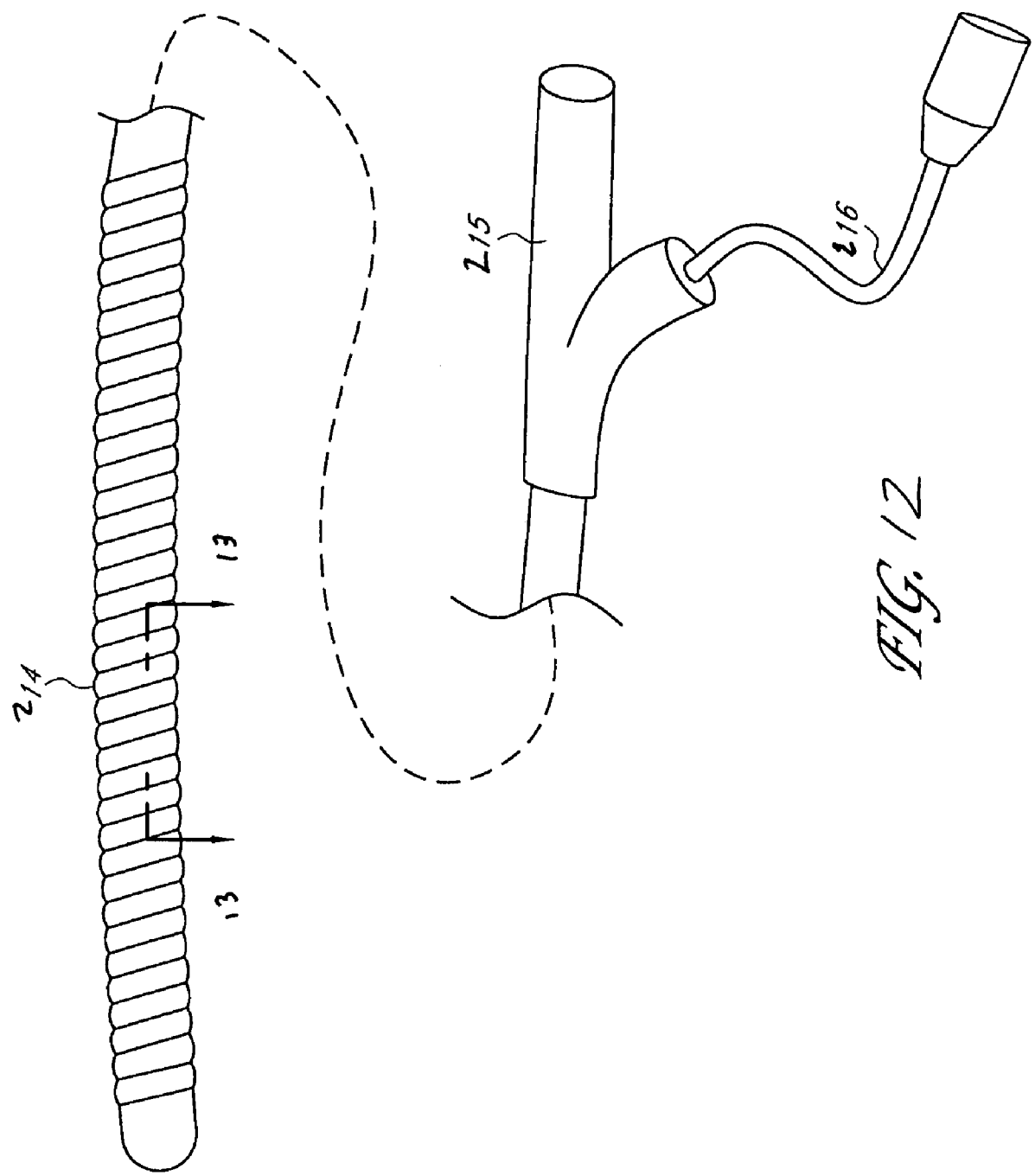
FIG. 12 illustrates a magnified view of an exemplary embodiment of a therapeutic element of a catheter usable with the resistive element system of FIG. 10.
Figure 13:
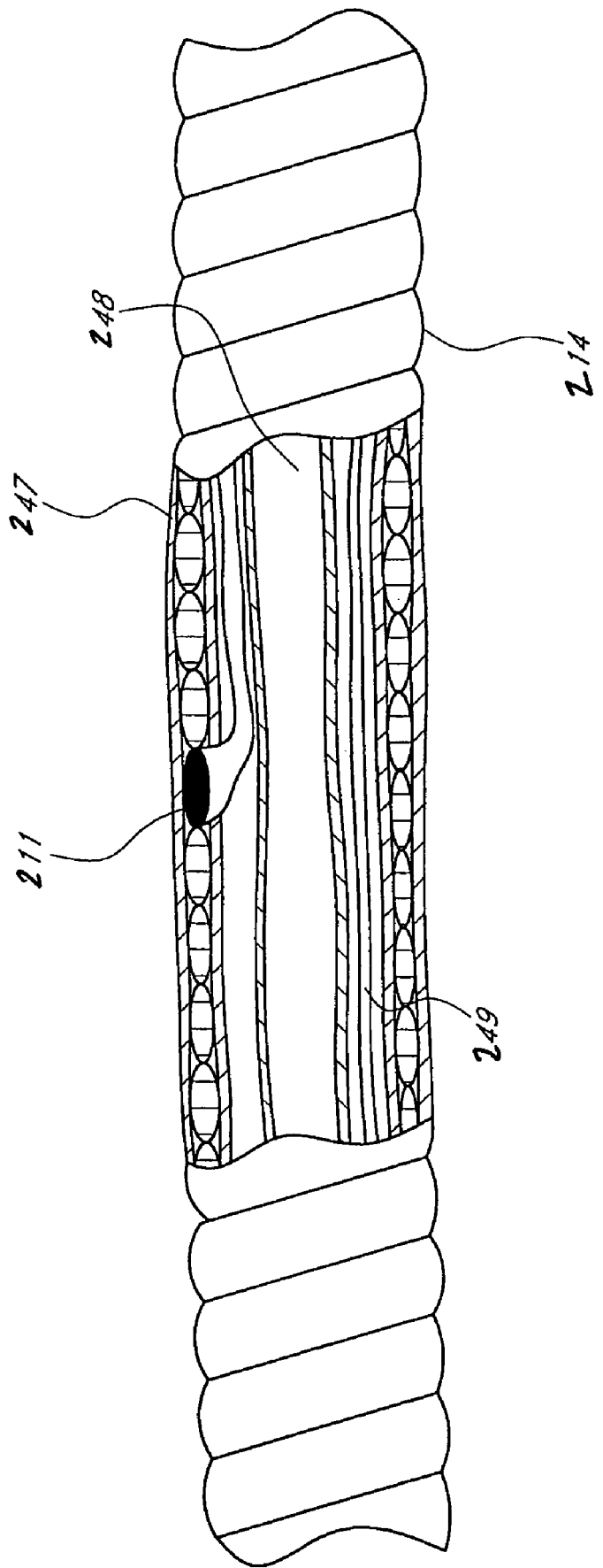
FIG. 13 illustrates a cross-sectional side view of the therapeutic element (i.e., working end) of the catheter of FIG. 12.

FIG. 12 illustrates a catheter with a cross-section 13—13 of the resistive element 214, which is further depicted in FIG. 13. In particular, FIG. 13 illustrates a detailed cross-sectional portion of the resistive element 214 and internal components of the catheter. As will be appreciated, the distance between the illustrated adjacent coils of the resistive element 214 may be of consistent or varied spacing.

The distal section of the catheter in FIG. 13 shows the resistive element 214 covered by a sleeve 247. In one embodiment, the sleeve 247 is a thin-walled tube from approximately 0.00025 inch to approximately 0.003 inch thick. In other embodiments, the sleeve 247 may have a wall thickness of less than 0.00025 inch or of more than 0.003 inch. In one embodiment, the sleeve 247 comprises PET (polyethylene terephthalate). In other embodiments, the sleeve 247 may comprise TEFLON®, polyimide or other thin-walled sleeve material that remains substantially stable for the desired temperature range. The material selection process of sleeve 247 may be determined by using polymers with nonconductive or electrically insulative properties.

FIG. 13 also shows an internal lumen 248 of the catheter, which communicates through an open lumen, such as from a distal tip to a proximal handle. In one embodiment, the lumen 248 is used for delivery of fluids, such as for example, saline, a venoconstrictor, sclerosant, high-impedance fluid, physiologic tissue adhesive, hydrogel, combinations of the same or the like. In addition, upon completion of treatment, a hydrogel may be exuded from the distal catheter end, allowing for substantially complete vessel occlusion. For example, the hydrogel may be biocompatible or bioresorbable. In other embodiments, the hydrogel may be displaced by the constriction of the HAS resulting from the thermal injury response, which results in substantially complete occlusion. In those sections of the HAS in which the fluid material has not completely compressed the HAS wall, the fluid material may be naturally resorbed by the body. In yet other embodiments, the lumen 248 may also accommodate a guide wire for catheter placement.

In certain embodiments, the resistive element 214 of the catheter is made of resistive wire that generates heat when an energy source (e.g., energy source 218 of FIG. 10) is connected and applied thereto. As shown in FIG. 13, the resistive element 214 comprises a wire having an oval-shaped cross-section. In other embodiments, the cross-section of the resistive element 214 may alternatively be rectangular, circular, or another geometrical cross-section. Preferably, the relative resistance or impedance of the resistive element 214 is designed to correlate to, or match, the energy source. For example, the resistance of resistive element 214 may be determined by a wire gage that relates to the catheter diameter, the energy required during treatment, and/or the energy source specifications. The resistive element 214 may comprise a wide variety of conductive materials, such as, for example, nickel chromium, copper, stainless steel, NITINOL®, ALUMEL®, combinations or alloys of the same and the like.

The resistive element 214 illustrated in FIG. 13 is a close-pitch (or closed-wind) coil (i.e., with substantially no inter-coil spacing). In one embodiment, an electrical connection, such as soldering at the proximal end and/or the distal end of the coil, couples the resistive element 214 to a signal wire 249. As shown in FIG. 13, the signal wire 249 is a distal return signal wire. For example, the signal wire 249 may run the internal length of the catheter to a connector cable. In one embodiment, the signal wire 249 extends from the proximal end of the coil. In such an embodiment, the signal wire 249 is preferably a larger gage copper wire (e.g., 28 to 34 gage) to reduce possible heating within the main body of the catheter.

In an embodiment, the resistive element 214 comprises a constant, closed-pitch coil. Alternatively, the resistive element 214 may have a varying pitch and/or a varying inter-coil spacing. For example, a varying coil pitch and/or spacing may be advantageously used to vary the heat output over the axial length of the resistive element 214. An axially (and/or radially) varying heat output from the resistive element 214 may be useful in providing a substantially uniform tissue and/or device temperature during treatment.

For example, such a variation in coil pitch may be advantageous in situations involving fluid flow within the HAS. In such embodiments, fluid tends to absorb heat output from the proximal portion of the resistive element 214 to a greater degree than heat output from the distal portion. Such may result in a reduction of the heat actually applied to the wall of the HAS adjacent to the proximal portion of the resistive element 214 relative to the central and distal sections. As the fluid flows past the proximal section of the resistive element 214, the fluid itself is heated. The heated fluid then flows across the middle and distal sections of the resistive element 214, thereby increasing the temperature of treatment for these sections.

Certain embodiments of the invention, intended to counteract this uneven heat distribution, comprise a close-pitch wind of the resistive element 214 in the proximal portion (implying a higher heat output in the proximal portion), while the middle and distal sections have a comparatively more open-pitch wind (i.e., the inter-coil spacing increases in the distal direction). This configuration advantageously decreases the heat output along portions of the coil in order to compensate for the added heat from the proximal adjacent sections. That is, the variable coil pitch may be used to correct for higher temperatures of the middle sections of the resistive element 214 in comparison with lower temperatures of the end sections of the resistive element 214. A thermally-insulating material (such a natural rubber, silicone, or an elastomer) may also be used to shield the internal lumen 248 from heating and/or to selectively reduce external heat transfer from the resistive element 214.

In another embodiment, portions of the resistive element 214 having a close-pitch wind are used to heat larger portions of a HAS (e.g., portions having a larger diameter) while portions of the resistive element 214 having an increased coil spacing are used to heat smaller portions of the HAS (e.g., portions having a smaller diameter).

In other embodiments of the invention, multiple wires are provided and energy is applied separately to each wire of a bifilar wire coil. For example, applying energy separately to each wire may be used to vary and control the power and heat transferred from the device to the HAS. In one embodiment, a single coil is used for a relatively smaller HAS, while a plurality of coils are used with a relatively larger HAS.

In another embodiment, a resistive element comprises multiple coils or electrodes, which are sequentially placed axially on the catheter shaft. In certain embodiments, each resistive element may be individually temperature controlled and/or may comprise a temperature sensor. Alternatively, the resistive elements may be used in a power control mode that relies on manual energy control.

Alternatively, in embodiments of the invention having multiple resistive elements, a temperature sensor is located on the most distal resistive element. For example, the most distal resistive element may be used for the initial treatment, and the successive coil electrodes may use the same and/or a predetermined energy-time profile.

In certain embodiments, a method of use of the resistive element includes multiplexing through each of the resistive elements. The term "multiplex" as used herein is a broad term and is used in its ordinary sense and includes, without limitation, the energizing or heating of at least one resistive element for a specific dwell time and cascading, or moving, to another resistive element until a final resistive element is reached or until a cycle is completed. In certain embodiments, the cycle may then be repeated until the complete treatment time is reached.

In one embodiment, to avoid overcooling a particular resistive element, the cycle time is of a shorter duration and/or the total number of resistive elements is limited. That is, in certain embodiments, a resistive element may be re-energized before substantial cooling takes place. In addition, in an embodiment, to increase the treatment zone the catheter may comprise multiple treatment zones, such as for example, groups of eight resistive elements. Each group of eight resistive elements may treat the wall of the HAS before energy is applied to the next group of resistive elements. Alternative modes of multiplexing may also be employed. For example, the number of adjacent resistive elements simultaneously energized may vary. Also, the entire cycle may re-start at the first energized resistive element or the most recent energized resistive element. Another mode of multiplexing may be accomplished while sensing the tissue impedance. Once a certain impedance level is achieved, the next set of resistive elements is then energized. In some embodiments, the controller is in communication with the catheter to control the multiplexing function based on input from other control parameters, such as for example, dwell time and temperature.

In an alternative embodiment, a resistive heating device can be configured such that the resistive heating element also acts as a resistance temperature device (RTD). Certain metals exhibit predictably varying electrical resistance properties at varying temperatures. If this relationship is known for a given resistive heating element, a temperature of the element can be determined by measuring an electrical resistance across it. Such a system may advantageously eliminate the need for additional thermocouples or other temperature sensing devices and/or may provide an independent sensing of temperature for high-temperature situations. The controller can be in communication with an RTD to detect electrical resistance properties in some embodiments.

In some embodiments, it is desirable to provide a heating element configured to treat a relatively short lengths of a HAS at successive intervals. Such an embodiment can be progressively moved through the HAS in a series of discrete steps from a first position to a final position in order to treat a desired length of the HAS. The process of moving a heating element through a HAS in a series of discrete steps during treatment is referred to herein as "indexing." In some embodiments, the controller can control the indexing of the catheter based on sensing one or more of the other control parameters described herein, such as, for example, temperature, power output, or flow rate.

A general indexing process may proceed by providing an elongate catheter with a relatively short-length heating element at a distal portion thereof. The heating element and/or catheter may be inserted through an introducer sheath into a HAS, such as, for example, a vein. The heating element is advanced to a distal-most position, and power is then applied thereto. The temperature of the subject heating element is allowed to ramp up or increase to a desired temperature and remains in place for a desired dwell time. Once the desired dwell time is reached (e.g., the treatment for the section is completed), the heating element can be powered down, and the element can be indexed proximally to a second position, at which point at least one of the ramp up, dwell, power down, and indexing procedures may be repeated.

FIGS. 14-16D illustrate embodiments of short-length heating elements and indexing systems. It should also be noted that the devices and structures discussed previously herein may also be used in an indexing system. For exemplary purposes, several of the following embodiments are described with reference to a coil-type resistive element.

Figures 14, 15:
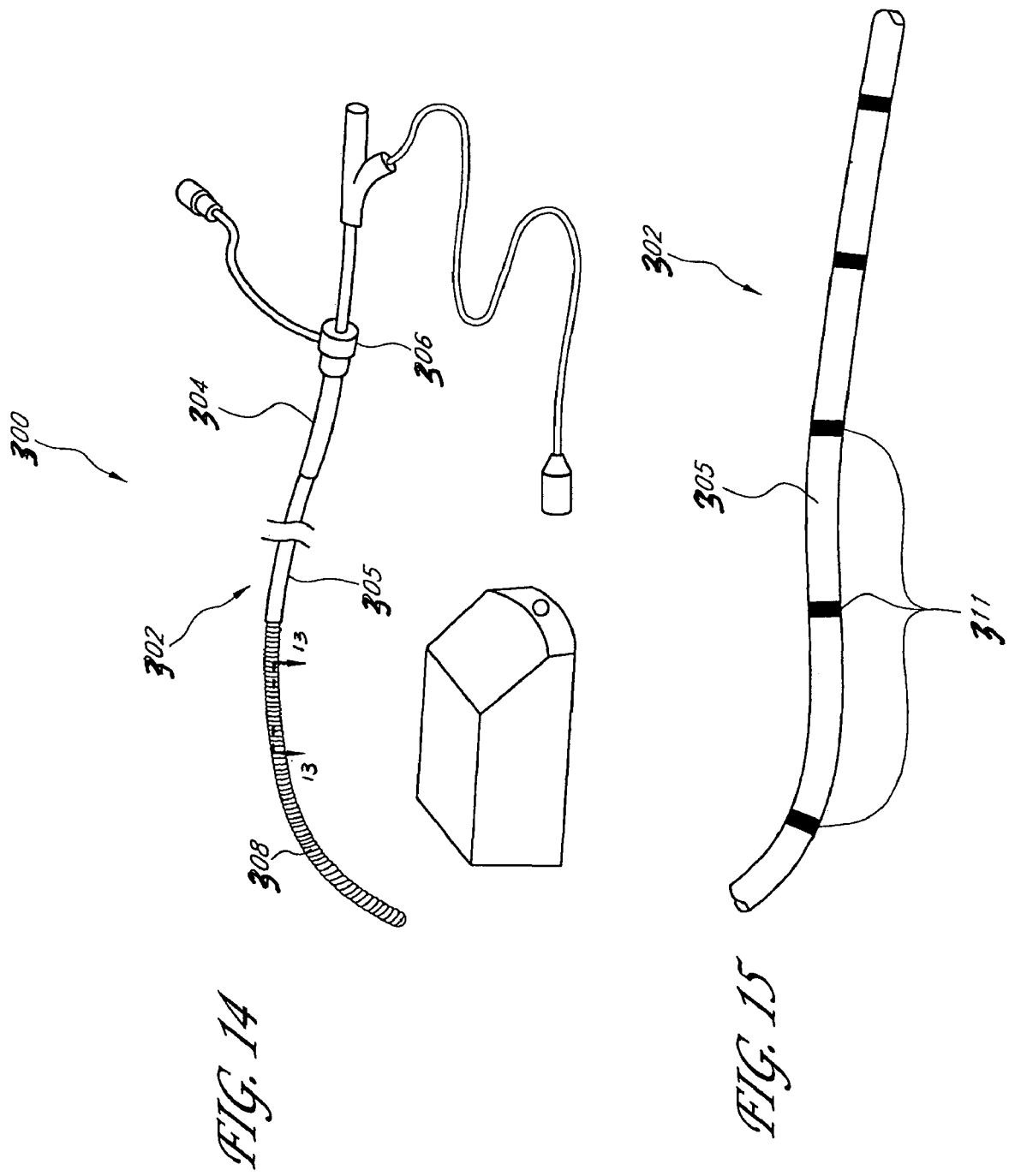
FIG. 14 illustrates an exemplary embodiment of an indexing treatment system for hollow anatomical structures, according to certain embodiments of the invention.
FIG. 15 illustrates an exemplary embodiment of a catheter having markings usable with an embodiment of an indexing treatment system for hollow anatomical structures.

For example, FIG. 14 illustrates one embodiment of an indexing HAS treatment system 300 comprising an elongate catheter 302 extending through an introducer sheath 304, which includes a hub 306, and a heating element 308 located at the distal end of the catheter shaft 305.

In certain embodiments, the heating element 308 is an electrically resistive heating element, including but not limited to any of those described elsewhere herein. For example, the heating element 308 may comprise a single, bifilar or other electrically resistive wire. FIG. 14 further illustrates an embodiment of the heating element 308 comprising a wire having tightly-wrapped coils around a hollow, elongate structure. Thus, the embodiment of FIG. 14 can include a heating element 308 in the form of a coil similar to that shown in partial section in FIG. 13 above. In other embodiments, the heating element 308 may comprise a loose, tight, or variable-pitch coil wound around a solid or hollow elongate structure.

In certain embodiments, the heating element 308 has a substantially short axial length. For example, in certain embodiments, the heating element 308 has a length of between approximately one centimeter and approximately ten centimeters. Such a length is believed to be particularly advantageous for embodiments utilizing manual, external compression to treat a HAS. In certain preferred embodiments, the length of the heating element 308 is approximately seven centimeters.

In certain embodiments, the heating energy delivered by the heating element 308 of the system 300 is less than 100 watts. In a more preferred embodiment usable in an indexing process, the heating energy delivered by the heating element 308 is between approximately five watts and twenty watts.

In certain embodiments, in order to accurately index the heating element 308, it is desirable to provide a means for repeatedly moving (or facilitating accurate, repeated movement of) the heating element 308 proximally within a HAS undergoing treatment by a desired distance. In some embodiments, the controller controls the movement of the catheter via one or more positioning devices described above. In certain embodiments, this desired distance is less than the overall length of the heating element 308 so as to effectively re-treat regions that may receive less heat energy as a result of an uneven heating profile along the axial length of the heating element 308. It may also be desirable to treat more than once an initial and/or final treatment region of the HAS in order to arrange for start-and endpoints of the indexing distances to correspond with catheter shaft markings or to arrange that, after the full series of indexed treatments, the final HAS treatment region is in substantial alignment with the end of the introducer sheath 304. In addition, in certain embodiments, the system 300 includes means for preventing the heating element 308 from being powered up while it is within the introducer sheath 304.

In certain embodiments, as illustrated for example in FIG. 15, the catheter shaft 305 may comprise a plurality of markings 311 along the axial length thereof in order to assist in visual verification of indexing positions. Such markings 311 advantageously assist a user in positioning and indexing the heating element of the catheter 302 during treatment. For example, the user may determine from the markings 311 how far the heating element should be retracted during a treatment interval. In some embodiments, the controller is in communication with an imaging device and/or a position sensor that can sense the relative position of the catheter based on the markings 311.

In certain embodiments, the physician uses the markings 311 to manually and selectively move the catheter 302 within a HAS of a patient. In some other embodiments, the controller automatically moves the catheter 302 within the HAS of a patient based on sensed control parameters. For example, the catheter 302 may have an associated therapeutic or heating element at the end thereof that extends approximately seven centimeters in length. In such an embodiment, the markings 311 may be spaced apart at approximately 6.5 centimeter intervals. When treating the patient, the physician may use the markings 311 to manually withdraw from the HAS the catheter 311 at 6.5 centimeter intervals between successive treatments of the HAS. Such a 6.5 cm movement can be performed by proceeding from a first state in which a first shaft marking 311 is aligned with a fixed reference point (e.g., the proximal edge of the introducer sheath hub 306 or other datum device as discussed in further detail below), then moving the catheter shaft 305 proximally (or distally) to reach a second state in which a proximally (or distally) adjacent second shaft marking 311 is aligned with the fixed reference point. In other embodiments, and as discussed in more detail below, a device may be used to automatically withdraw the catheter at the predetermined intervals indicated by the markings 311.

FIGS. 16A-16D depict one embodiment of the HAS treatment system 300 and a method of its use to treat a vein, such as the great saphenous vein (GSV) as depicted, near its junction with the femoral vein (FV), at the sapheno-femoral junction (SFJ). In other embodiments, of the invention, the system 300 can be used to treat other HASs, such as other veins.

Figure 16A:
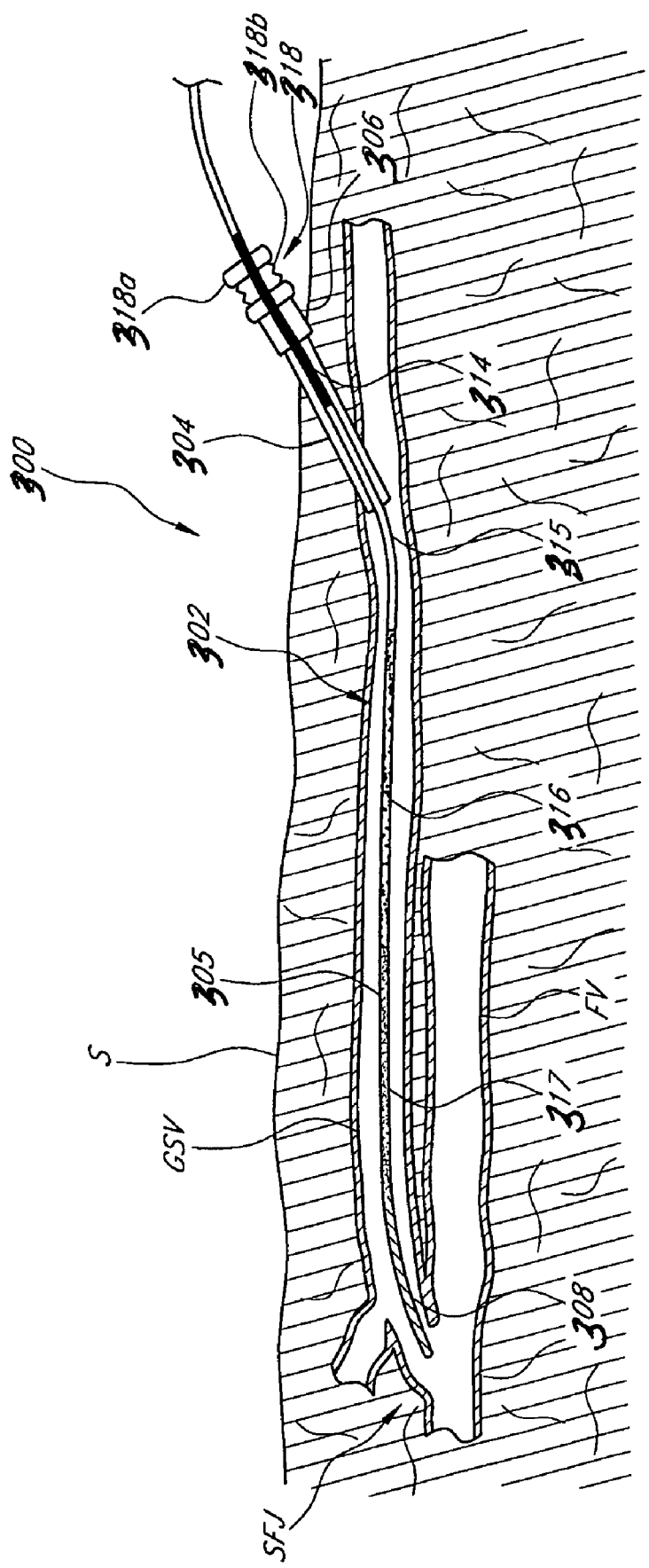
FIGS. 16A-16D illustrate another exemplary embodiment of a catheter usable with an embodiment of an indexing treatment system for hollow anatomical structures.

In certain embodiments, and as depicted in FIG. 16A, the introducer sheath 304 is first inserted through the patient's skin S and manipulated until the distal end of the sheath 304 is within the lumen of the GSV, and the hub 306 remains outside the skin surface. Once the sheath 304 is in place, the catheter 302 is passed distally through the lumen of the sheath 304, and into the GSV until the distal tip of the heating element 308 is positioned at or near the SFJ, as shown in FIG. 16A. The position of the heating element 308 can be monitored or confirmed using appropriate extracorporeal vision techniques, such as, for example, ultrasonic imaging. In some embodiments, the controller is in communication with the imaging device to detect one or more control parameters, such as for example positional velocity and/or dwell time.

In the embodiment of FIGS. 16A-16D, the catheter shaft 305 is marked with first, second, third and fourth marking sections 314, 315, 316, 317, which are marked on the shaft 305 in any of the arrangements set forth herein (e.g., alternate colored and/or cross-hatched sections, or a series of tick marks spaced apart from each other by the desired indexing distance) so as to make the distal and proximal edges of each section 314, 315, 316, 317 easily visible by the user. Thus, the user can observe the marking section(s) to determine the relative position of the heating element 308 within a HAS and/or with respect to the introducer sheath 304. Preferably, the axial length of each section 314, 315, 316, 317 is approximately equal to the length of the heating element 308, less any intended overlap distance between treatments. In one preferred embodiment, the heating element 308 is seven centimeters in length and each section 314, 315, 316, 317 is 6.5 cm in length. The shaft 305 can be varied in length so as to include more or fewer sections than the four depicted in FIGS. 16A-16D.

The sheath 304 depicted in FIGS. 16A-16D includes a longitudinally adjustable datum device or reference point indicator 318, which can be employed to provide a fixed reference for the position of the shaft 305 and heating element 308 as discussed in further detail below. Preferably connected to the proximal end of the hub 306, the reference point indicator 318 comprises a reference point 318a which is longitudinally moveable relative to the hub 306 via an adjustable section 318b, which in the depicted embodiment comprises an accordion section. Alternatively, the adjustable section 318b can comprise a threaded cylinder or other threaded member (not shown) which engages threads on the hub 306 to facilitate longitudinal movement of the reference point 318a via rotation of the adjustable section 318b relative to the hub 306. However implemented, the adjustable section 318b is preferably transparent, or includes a transparent window or an opening to permit the user to see the portion of the catheter shaft 305 that passes through the adjustable section 318b proximal of the hub 306.

Figure 16B:
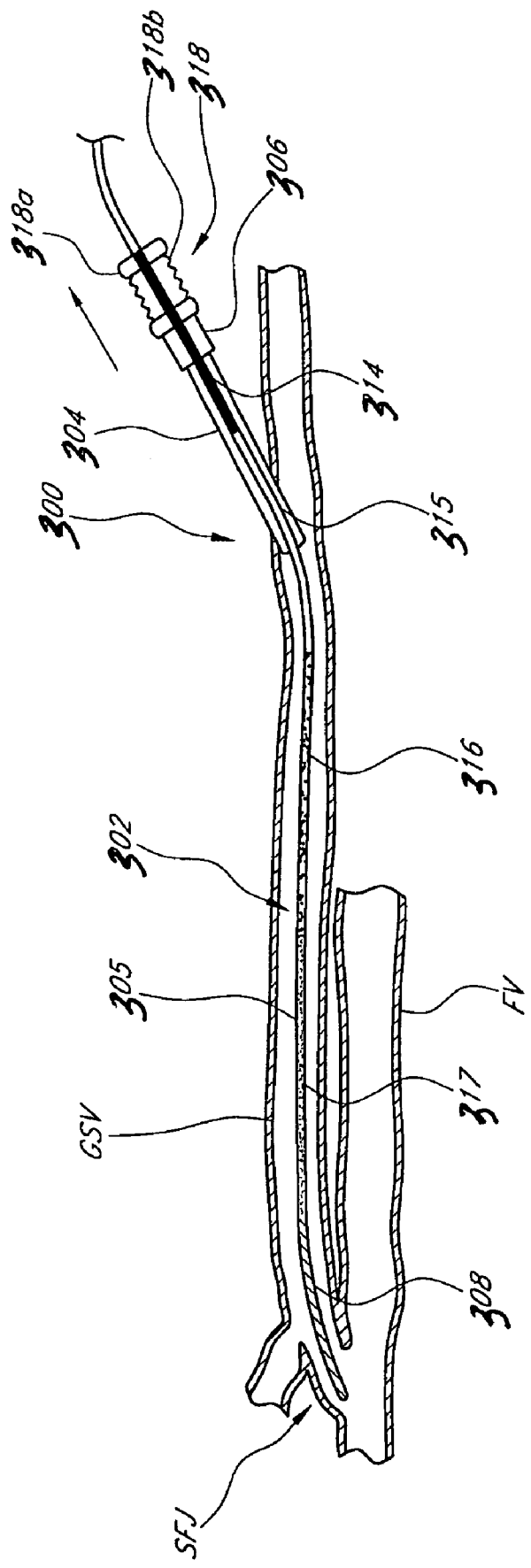

With resumed reference to the method depicted in FIGS. 16A-16D, once the catheter 302 is in place in the GSV with the heating element 308 near the SFJ (FIG. 16A), the user adjusts the reference point indicator 318 by aligning the reference point 318a with the proximal edge of the first marking section 314. In FIG. 16B, this is depicted as a proximal movement of the reference point 318a relative to the catheter shaft 305, accomplished by longitudinally stretching or extending the accordion section and then fixing the reference point 318a in the correct position by any suitable means. Where the adjustable section 318b comprises a threaded cylinder or the like, the cylinder is rotated until the reference point 318a reaches the correct position, where it is fixed in position.

Figure 16C:
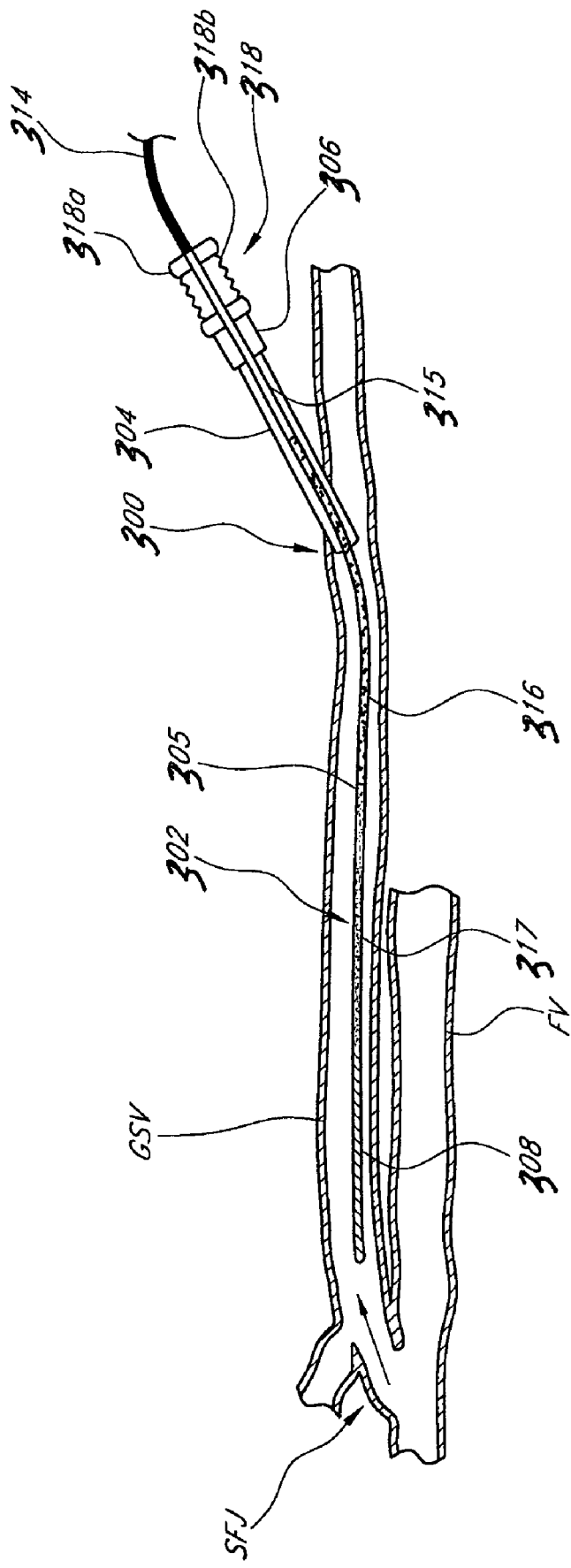
Figure 16D:
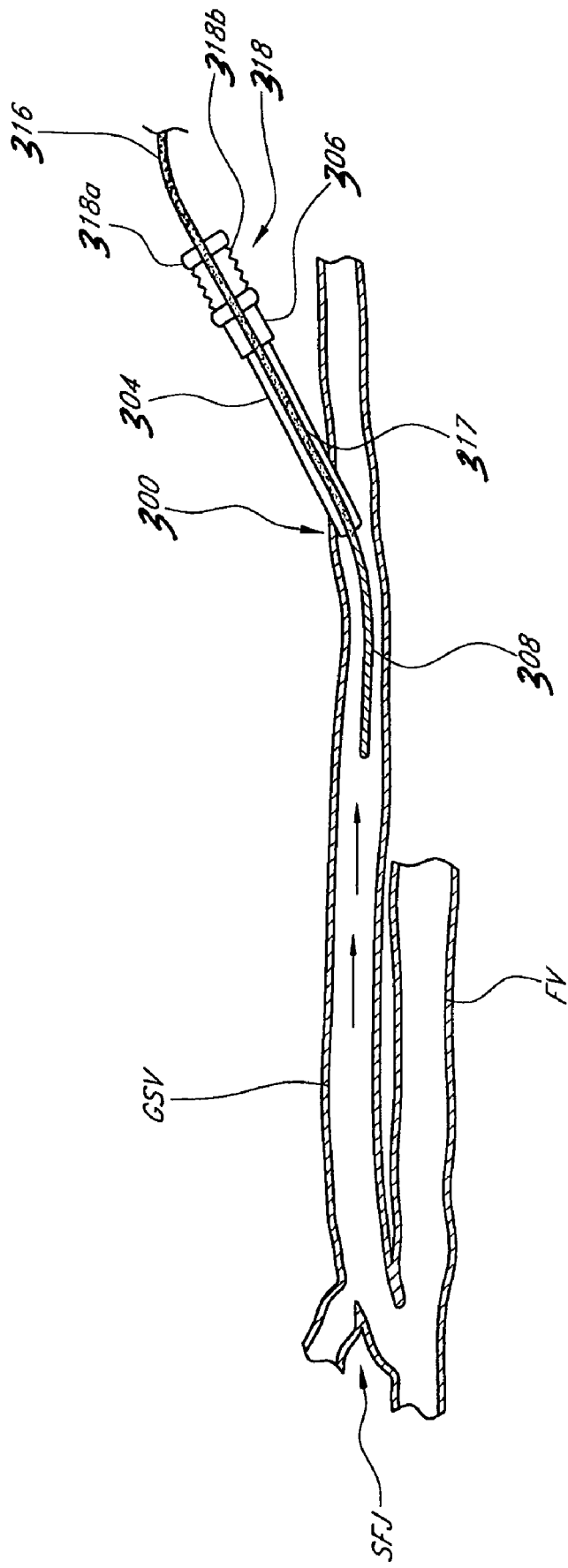

The system 300 is now ready for use in treating the GSV as follows. FIG. 16B shows the heating element 308 in an initial treatment position near the SFJ. At this point, the user and/or the controller activates the heating element 308 by cycling through the steps of powering up the heating element 308, dwelling at a power or temperature state (or series of states), and then powering down the heating element 308. Having completed the treatment cycle for an initial, distal section of the GSV, the user and/or controller then moves the catheter shaft 305 and heating element 308 proximally by the desired indexing distance (e.g., 6.5 cm), by moving the shaft proximally until the proximal edge of the second marking section 315 is aligned with the reference point 318a (FIG. 16C). The user and/or controller then repeats the treatment cycle with the heating element 308. Following the treatment cycle, the user and/or controller again moves the shaft 305 and heating element 308 proximally by the indexing distance, pulling the shaft proximally until the proximal edge of the third marking section 316 is aligned with the reference point 318a.

This sequence of treatment cycle-index-treatment cycle is repeated until the desired length of the GSV (or other vein or HAS) has been treated, at which point the catheter 302 and introducer sheath 304 are removed from the treatment area.

In certain embodiments, the fourth or distal-most marking section 317 indicates a "stop treatment zone," which can be employed to prevent the heating element 308 from being withdrawn too far (e.g., into the introducer sheath 304). For example, the fourth marking section 317 may comprise a band of a solid or patterned color such as red, yellow or other color or pattern that contrasts with the base color or pattern of the catheter shaft 305.

Furthermore, when implemented as a stop-treatment marker, the fourth or distal-most marking section 317 preferably has a length that is substantially equal to the length of the introducer sheath 304 (rather than having a length equal to the desired indexing distance as discussed above), which generally includes, but is not limited to, the following lengths: five, seven and eleven centimeters. In certain embodiments, a plurality of distinct stop-treatment markers may be used on a single shaft 305, the plurality of stop-treatment markers corresponding to the various lengths of introducer sheaths usable with the catheter 302.

Thus, when used as a stop-treatment marker, if the proximal edge of the fourth or distal-most marking section 317 is pulled out of the proximal end of the introducer sheath 304 (see FIG. 16D), the user and/or controller will know that the heating element 308 is positioned within the introducer sheath 304. The user and/or controller can then push the catheter 302 distally until the stop-treatment marker is positioned within the hub of the introducer sheath 304, thus avoiding damage to the sheath 304 and/or heating element 308.

In certain embodiments, the indexing process described with reference to FIGS. 16A-16D allows a user and/or controller to treat selected segments of a HAS for successive periods of time. Furthermore, the markings 314-317 and the reference point indicator 318 of the introducer sheath 304 advantageously allow the user and/or controller to determine the relative position of the heating element 308 within the HAS and/or with respect to the introducer sheath 304 through a means external to the body of the patient.

Although described with reference to particular embodiments, other types or forms of markings may be used with embodiments of the HAS indexing system described herein. For example, in certain embodiments, it may be desirable to provide a unique marker to indicate a final, proximal-most, indexed position so that the corresponding heating element remains spaced from the introducer sheath by a sufficient distance to prevent the sheath from melting.

Certain methods of using an indexing HAS treatment system will now be described. The methods described herein can employ any suitable device described above or otherwise known to the skilled artisan. For example, in one embodiment, an indexing method can comprise inserting a heating element with a length of about five to about seven cm into a distal-most section of a HAS to be treated. Power can then be applied to the heating element for a desired length of time to treat the segment of the HAS adjacent to the heating element. After a desired dwell time, the power supply to the heating element can be reduced or shut off. With the power off (or substantially reduced), the heating element may then be indexed proximally (i.e., the heating element can be moved proximally until the distal end of the heating element is adjacent to the proximal end of the treated segment of the HAS).

An example of an index treatment includes treatment at a temperature between approximately 80° C. and approximately 95° C. for a dwell time of approximately twenty seconds or less. In a more preferred embodiment, the preferred index treatment is performed at approximately 80° C. for a dwell time of approximately twenty seconds. The ramp time to temperature may be approximately ten seconds or less, with a preferred time of approximately five seconds or less. In certain embodiments, the intent of a short ramp time is to advantageously reach and maintain the treatment temperature quickly in order to apply heat to the HAS in a local manner.

Once a section is treated, the distal therapeutic portion of the catheter is moved to the adjacent section. In certain embodiments, the catheter has an overlap portion of approximately one centimeter or less to substantially reduce or eliminate the number of under-treated sections or gaps as mentioned earlier. This process is repeated until the treatment of the HAS is complete. In other embodiments, higher temperatures such as, for example, 95° C., at a shorter dwell time are also possible depending on circumstances of the treatment. In yet other embodiments, the treatment process may comprise a multi-step heating process. For example, the HAS may be treated at a first temperature (e.g., 95° C.) for a first portion of the process and a second temperature (e.g., 80° C.) for a second portion of the process.

Except as further described herein, any of the catheters disclosed herein may, in some embodiments, be similar to any of the catheters described in U.S. Pat. No. 6,401,719, issued Jun. 11, 2002, entitled "METHOD OF LIGATING HOLLOW ANATOMICAL STRUCTURES"; or in U.S. Pat. No. 6,179,832, issued Jan. 30, 2001, titled "EXPANDABLE CATHETER HAVING TWO SETS OF ELECTRODES"; or in U.S. patent application Ser. No. 11/222,069, filed Sep. 8, 2005, entitled "METHODS AND APPARATUS FOR TREATMENT OF HOLLOW ANATOMICAL STRUCTURES." In addition, any of the catheters disclosed herein may, in certain embodiments, be employed in practicing any of the methods disclosed in the above-mentioned U.S. Pat. Nos. 6,401,719 or 6,179,832, or the above-mentioned U.S. patent application Ser. No. 11/222,069 filed Sep. 8, 2005. The entirety of each of these patents and application is hereby incorporated by reference herein and made a part of this specification.

While certain embodiments of the inventions have been described, these embodiments have been presented by way of example only, and are not intended to limit the scope of the disclosure. Indeed, the novel methods and systems described herein may be embodied in a variety of other forms; furthermore, various omissions, substitutions and changes in the form of the methods and systems described herein may be made without departing from the spirit of the disclosure.

What is claimed is:

1. A method of treating a hollow anatomical structure, comprising:
   employing a treatment device sized for insertion into a peripheral blood vessel and having a therapeutic element and a sensor, the treatment device being configured for connection to a controller for communication with the treatment device and with the sensor; and
   in the controller,
   (a) providing a processor;
   (b) establishing a blood vessel thermal injury value between a minimum thermal injury value capable of effecting an efficacious treatment and a maximum thermal injury value capable of effecting a safe treatment, the blood vessel thermal injury value related to at least two treatment parameters according to a known relationship that is recorded in the processor, the known relationship comprising a first series of distinct values for the first parameter that each have a corresponding specific value in a series of values for the second parameter;
   (c) determining a value for a first treatment parameter based on the established blood vessel thermal injury value; and
   (d) controlling operation of the treatment device by manipulating the value of a second treatment parameter that has the known relationship to the first treatment parameter, in order to achieve the determined first treatment parameter and thereby achieve the blood vessel thermal injury value that has been established for safely and efficaciously treating the blood vessel.

2. The method of claim 1, wherein establishing a blood vessel thermal injury value comprises establishing a user-input blood vessel thermal injury value.

3. The method of claim 2, wherein establishing a blood vessel thermal injury value comprises establishing a user-input range of acceptable blood vessel thermal injury values.

4. The method of claim 1, wherein the treatment device comprises a catheter with an electrode array at or near the distal end of the catheter.

5. The method of claim 4, further comprising causing the blood vessel to shrink by delivering power to the electrode array.

6. The method of claim 1, wherein the treatment device comprises a catheter with a heating coil located at or near the distal end of the catheter.

7. The method of claim 6, further comprising causing the blood vessel to shrink by delivering power to the heating coil.

8. The method of claim 1, further comprising sensing the first parameter with the sensor.

9. The method of claim 1, wherein the first treatment parameter is treatment temperature.

10. The method of claim 9, wherein the second treatment parameter is a dwell time of the therapeutic element.

11. The method of claim 10, wherein the treatment device comprises a catheter with a heating coil located at or near the distal end of the catheter, further comprising causing the blood vessel to shrink by delivering power to the heating coil.

12. The method of claim 1, wherein the blood vessel thermal injury value is computed based on the concentration of undamaged tissue after treatment with the treatment device.

13. The method of claim 1, wherein the first treatment parameter is a level of power delivered to the therapeutic element, a positional velocity of the therapeutic element, a dwell time of the treatment element, or a flow rate of a fluid delivered to the blood vessel via the treatment device.

14. The method of claim 1, wherein the second treatment parameter is a treatment temperature, a level of power delivered to the therapeutic element, a positional velocity of the therapeutic element, or a flow rate of a fluid delivered to the blood vessel via the treatment device.

15. The method of claim 1, wherein the known relationship can be expressed as a non-zero function in the two-dimensional space described by the two parameters.

16. The method of claim 1, wherein providing a processor comprises providing a computer system.

17. The method of claim 1, wherein the processor is part of the controller.

18. A system for treating a blood vessel, the system comprising:

a treatment device sized for insertion into a peripheral blood vessel, the treatment device having an elongate shaft with a therapeutic element located at or near the distal end of the shaft;

a controller in communication with the treatment device, the controller having a memory and being configured to:

(a) establish a blood vessel thermal injury value between a minimum thermal injury value capable of effecting an efficacious treatment and a maximum thermal injury value capable of effecting a safe treatment, the blood vessel thermal injury value related to at least two treatment parameters according to a known relationship that is recorded in the memory, the known relationship comprising first series of distinct values for the first parameter that each have a corresponding specific value in a series of values for the second parameter;

(b) determine a value for a first treatment parameter based on the established blood vessel thermal injury value; and (c) control operation of the treatment device by manipulating the value of a second treatment parameter that has a known functional relationship to the first treatment parameter, in order to achieve the determined first treatment parameter and thereby achieve the blood vessel thermal injury value that has been established for safely and efficaciously treating the blood vessel.

19. The system of claim 18, wherein the established blood vessel thermal injury value comprises a user-input blood vessel thermal injury value.

20. The system of claim 18, wherein the established blood vessel thermal injury value comprises a user-input range of acceptable blood vessel thermal injury values.

21. The system of claim 18, wherein the treatment device comprises a catheter with an electrode array at or near the distal end of the catheter.

22. The system of claim 21, wherein the controller is further configured to deliver sufficient power to the electrode array to cause the blood vessel to shrink.

23. The system of claim 18, wherein the treatment device comprises a catheter with a heating coil located at or near the distal end of the catheter.

24. The system of claim 23, wherein the controller is further configured to deliver sufficient power to the heating coil to cause the blood vessel to shrink.

25. The system of claim 18, wherein the controller is further configured to sense the first parameter with the sensor.

26. The system of claim 18, wherein the first treatment parameter is treatment temperature.

27. The system of claim 26, wherein the second treatment parameter is a dwell time of the therapeutic element.

28. The system of claim 27, wherein the treatment device comprises a catheter with a heating coil located at or near the distal end of the catheter, further comprising causing the blood vessel to shrink by delivering power to the heating coil.

29. The system of claim 18, wherein the blood vessel thermal injury value is computed based on the concentration of undamaged tissue after treatment with the treatment device.

30. The system of claim 18, wherein the first treatment parameter is a level of power delivered to the therapeutic element, a positional velocity of the therapeutic element, a dwell time of the treatment element, or a flow rate of a fluid delivered to the blood vessel via the treatment device.

31. The system of claim 18, wherein the second treatment parameter is a treatment temperature, a level of power delivered to the therapeutic element, a positional velocity of the therapeutic element, or a flow rate of a fluid delivered to the blood vessel via the treatment device.

32. The system of claim 18, wherein the known relationship can be expressed as a non-zero function in the two-dimensional space described by the two parameters.

33. The system of claim 18, wherein the controller having a memory comprises a processor.

34. The system of claim 33, wherein the processor comprises a computer system.

* * * * *

UNITED STATES PATENT AND TRADEMARK OFFICE
CERTIFICATE OF CORRECTION

PATENT NO. : 7,842,076 B2  
APPLICATION NO. : 11/313512  
DATED : November 30, 2010  
INVENTOR(S) : Zikorus et al.

Page 1 of 1

It is certified that error appears in the above-identified patent and that said Letters Patent is hereby corrected as shown below:

At page 1, second column, line 2 under OTHER PUBLICATIONS, delete "edoluminal" and insert -- endoluminal --, therefor.

At page 2, second column, line 36, delete "Dimenson During RF Cardiac" and insert -- Dimension --, therefor.

At column 11, line 8, delete the second instance of "input".

At column 11, line 53 (Approx.), delete "$H_2(PV)=\alpha_4 PV^2+\beta_4 \cdot PV+\kappa_2$" and insert -- $H_2(PV)=\alpha_4 \cdot PV^2+\beta_4 \cdot PV+\kappa_2$ --, therefor.

Signed and Sealed this  
Twenty-fifth Day of January, 2011

David J. Kappos  
*Director of the United States Patent and Trademark Office*